(12) United States Patent
Horvath et al.

(10) Patent No.: US 8,210,829 B2
(45) Date of Patent: Jul. 3, 2012

(54) TWO-STAGE ROTODYNAMIC BLOOD PUMP WITH AXIALLY MOVABLE ROTOR ASSEMBLY FOR ADJUSTING HYDRAULIC PERFORMANCE CHARACTERISTICS

(75) Inventors: David Horvath, Euclid, OH (US); Leonard A. R. Golding, Chargrin Falls, OH (US); Alex Massiello, Chesterland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/720,953

(22) Filed: Mar. 10, 2010

(65) Prior Publication Data

US 2010/0168848 A1    Jul. 1, 2010

Related U.S. Application Data

(63) Continuation-in-part of application No. 11/789,205, filed on Apr. 24, 2007, now Pat. No. 7,704,054.

(60) Provisional application No. 60/795,096, filed on Apr. 26, 2006.

(51) Int. Cl.
*F04D 27/00* (2006.01)
*F04D 29/042* (2006.01)
*F04D 29/40* (2006.01)
*A61M 1/10* (2006.01)

(52) U.S. Cl. ........ 417/350; 415/131; 417/359; 417/420; 417/423.14; 623/3.13

(58) Field of Classification Search ................ 417/350, 417/365, 423.5, 423.7, 359, 420, 423.14; 623/3.13; 418/21; 415/2.1, 14, 34, 93, 113, 131, 132, 140, 161, 163, 173.2
See application file for complete search history.

(56) References Cited

U.S. PATENT DOCUMENTS 1,896,219 A * 2/1933 William ................. 415/131
(Continued)

FOREIGN PATENT DOCUMENTS

DE    27 33 631 A1    2/1979
(Continued)

OTHER PUBLICATIONS

Qian, K.X. et al, A Novel Permanent Maglev Impeller TAH: Most Requirements on Blood Pumps have been Satisfied, Journal of Biomaterials Applications, vol. 18, Jul. 2003, pp. 53-61.*

(Continued)

*Primary Examiner* — Charles Freay
*Assistant Examiner* — Nathan Zollinger
(74) *Attorney, Agent, or Firm* — Tarolli, Sundheim, Covell & Tummino LLP

(57) ABSTRACT

A pump (10) includes a housing, a stator (20) supported in the housing, and a rotor assembly (30). The rotor assembly (30) includes a rotor (32) supported in the housing for rotation relative to the stator (20) about an axis (12). The rotor assembly (30) also includes a first impeller (34) operatively coupled to a first axial end of the rotor (32) for rotation with the rotor about the axis (12). The rotor assembly further includes a second impeller (36) operatively coupled to a second axial end of the rotor (32), opposite the first axial end, for rotation with the rotor about the axis (12). The rotor assembly (30) is movable along the axis (12) relative to the housing to adjust hydraulic performance characteristics of the pump (10).

26 Claims, 17 Drawing Sheets

U.S. PATENT DOCUMENTS

| | | | |
|---|---|---|---|
| 1,959,106 A * | 5/1934 | Messing | 415/131 |
| 3,410,218 A | 11/1968 | Fivel | |
| 3,783,453 A * | 1/1974 | Bolie | 623/3.16 |
| RE28,742 E | 3/1976 | Rafferty et al. | |
| 4,355,954 A | 10/1982 | Wilson | |
| 4,381,901 A | 5/1983 | Labudde | |
| 4,392,777 A * | 7/1983 | Huttlin | 415/131 |
| 4,589,822 A * | 5/1986 | Clausen et al. | 415/174.3 |
| 4,752,183 A * | 6/1988 | Sakurai | 415/12 |
| 4,867,633 A | 9/1989 | Gravelle | |
| 5,055,005 A * | 10/1991 | Kletschka | 417/356 |
| 5,102,295 A | 4/1992 | Pope | |
| 5,320,482 A | 6/1994 | Palmer et al. | |
| 5,368,439 A * | 11/1994 | Piazza | 415/131 |
| 5,507,629 A * | 4/1996 | Jarvik | 417/423.3 |
| 5,695,471 A | 12/1997 | Wampler | |
| 5,725,357 A * | 3/1998 | Nakazeki et al. | 417/18 |
| 5,863,179 A | 1/1999 | Westphal et al. | |
| 6,074,180 A | 6/2000 | Khanwilkar et al. | |
| 6,171,078 B1 | 1/2001 | Schob | |
| 6,193,473 B1 | 2/2001 | Mruk et al. | |
| 6,220,832 B1 * | 4/2001 | Schob | 417/423.5 |
| 6,244,835 B1 | 6/2001 | Antaki et al. | |
| 6,394,769 B1 | 5/2002 | Bearnson et al. | |
| 6,422,838 B1 * | 7/2002 | Sloteman | 417/423.5 |
| 6,511,298 B2 | 1/2003 | Takura et al. | |
| 6,551,058 B2 * | 4/2003 | Nowack | 415/140 |
| 6,595,762 B2 | 7/2003 | Khanwilkar et al. | |
| 6,619,935 B1 | 9/2003 | Kluth et al. | |
| 6,638,031 B1 * | 10/2003 | Humburg | 417/313 |
| 6,672,846 B2 | 1/2004 | Rajendran et al. | |
| 6,746,416 B2 * | 6/2004 | Hubbard et al. | 604/6.11 |
| 7,435,059 B2 * | 10/2008 | Smith et al. | 417/26 |
| 7,704,054 B2 * | 4/2010 | Horvath et al. | 417/213 |
| 2007/0253842 A1 | 11/2007 | Horvath et al. | |

FOREIGN PATENT DOCUMENTS

| | | |
|---|---|---|
| GB | 1 115 210 A | 5/1968 |
| JP | 54-020214 A | 2/1979 |
| JP | 59-133735 A | 9/1984 |
| JP | 63-189692 A | 8/1988 |
| WO | WO 2004098677 A1 * | 11/2004 |
| WO | WO 2006053384 A1 * | 5/2006 |

OTHER PUBLICATIONS

Qian et al., "A Novel Permanent Maglev Impeller TAH: Most Requirements on Blood Pumps Have Been Satisfied", *Journal of Biomaterials Applications*, vol. 18, Jul. 2003, pp. 53-61.

Frazier et al., "Total Heart Replacement with Dual Centrifugal Ventricular Assist Devices", *ASAIO Journal 2005*, vol. 51, pp. 224-229.

The International Preliminary report dated Apr. 20, 2010, 8 pgs.

* cited by examiner

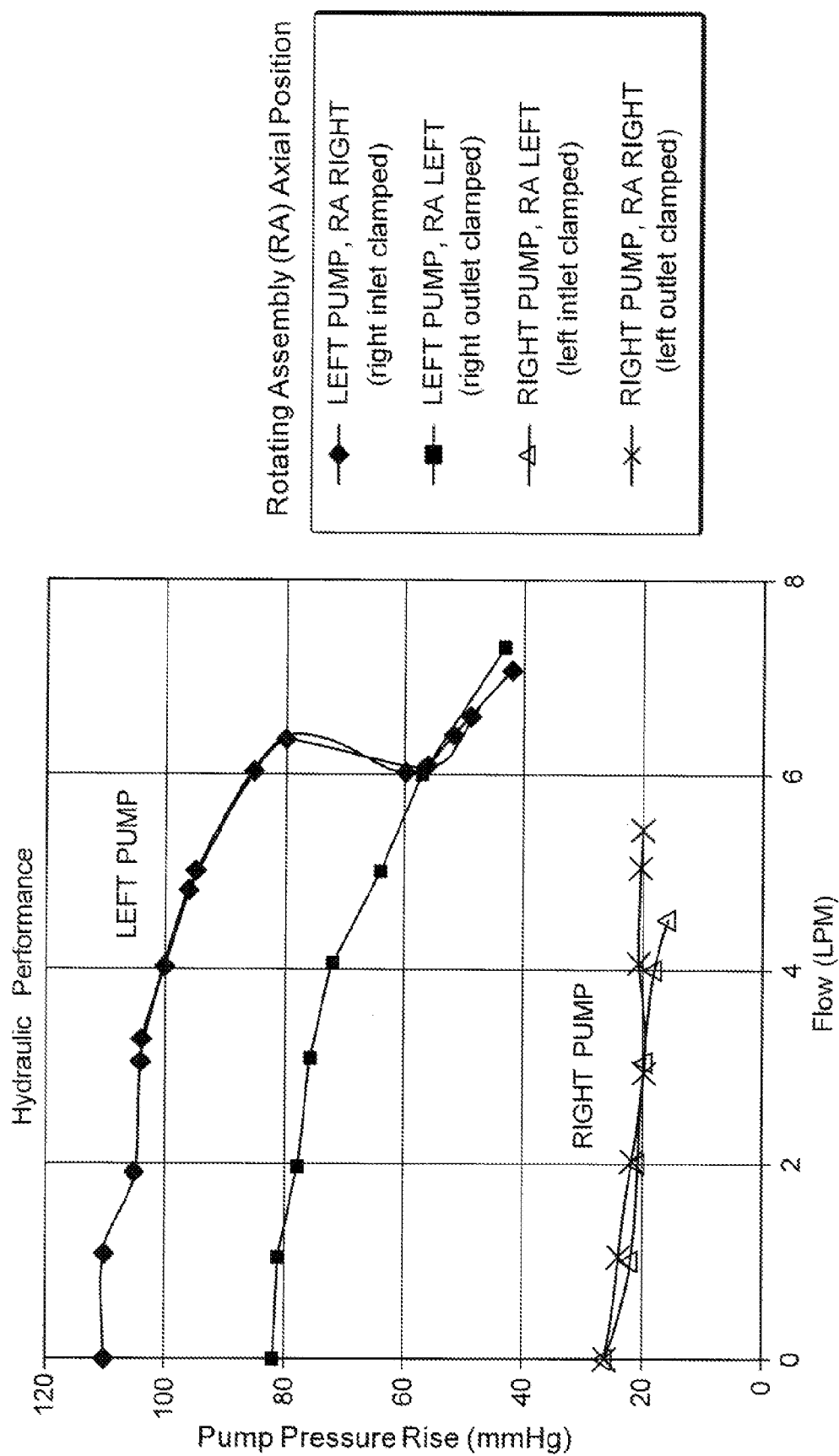

TWO-STAGE ROTODYNAMIC BLOOD PUMP WITH AXIALLY MOVABLE ROTOR ASSEMBLY FOR ADJUSTING HYDRAULIC PERFORMANCE CHARACTERISTICS

RELATED APPLICATIONS

This application is a continuation-in-part of U.S. application Ser. No. 11/789,205, filed on Apr. 24, 2007, now U.S. Pat. No. 7,704,054 which claims the benefit of U.S. Provisional Application Ser. No. 60/795,096, filed on Apr. 26, 2006.

TECHNICAL FIELD

The present invention relates to a pump that may be used in fluid handling applications where two fluid streams are to be balanced. More particularly, the present invention relates to a two-stage rotodynamic pump configuration for providing pulsatile, continuous flow, blood pumping performance.

BACKGROUND OF THE INVENTION

Congestive heart failure (CHF) is an increasingly common cause of cardiovascular disability and premature death. Despite advances in medical therapy, heart transplant is the primary course of action for treating patients with end-stage congestive heart failure. Because the availability of donor organs is limited, however, CHF patients may be forced to wait until a suitable donor organ is located. Blood pumping devices, referred to as ventricular assist devices (VADs) and total artificial hearts (TAH), can be used as a bridge-to-transplant option in order to save patients with CHF and other cardiac conditions who otherwise would not survive until a suitable donor organ is located. Ultimately, such blood pumping devices will become viable as permanent or long-term alternatives to transplant.

SUMMARY OF THE INVENTION

The present invention relates to a valveless, sensorless, pulsatile, continuous flow total artificial heart that can self balance left and right circulation, without electronic intervention, by acting as an inlet pressure balancing regulator as it pumps. Left and right circulations are impelled via a single moving part, which revolves within a brushless, sensorless DC motor winding. This rotating assembly is free to move axially in response to the hydraulic environment, thereby changing clearances in the two opposed rotodynamic pumping stages, affecting relative performance to balance the inlet pressures. In an alternate embodiment, external electronic control is employed to control the position of the rotating assembly via an electromotive force, such as a solenoid-type element. The pump configurations of the present invention may also be applied to other fluid handling applications where inlet pressure balancing is desired.

The present invention relates to a blood pump that includes a housing, a stator supported in the housing, and a rotor assembly. The rotor assembly includes a rotor supported in the housing for rotation relative to the stator about an axis. The rotor assembly also includes a first impeller operatively coupled to a first axial end of the rotor for rotation with the rotor about the axis. The rotor assembly further includes a second impeller operatively coupled to a second axial end of the rotor, opposite the first axial end, for rotation with the rotor about the axis. The rotor assembly is movable along the axis relative to the housing to adjust hydraulic performance characteristics of the pump.

The present invention also relates to a blood pump that includes a motor that includes a stator and a rotor rotatable about an axis relative to the stator. A first pump stage includes a first pump housing and a first impeller rotatable with the rotor about the axis in the first pump housing. A second pump stage includes a second pump housing and a second impeller rotatable with the rotor about the axis in the second pump housing. The blood pump is adapted to adjust the axial position of the first impeller in the first housing and the axial position of the second impeller in the second housing to adjust hydraulic performance characteristics of the first and second pump stages. Axial movement of the first and second stages is equal and opposite.

The present invention also relates to a blood pump that includes a motor comprising a stator and a rotor rotatable about an axis relative to the stator. The blood pump also includes a first pump stage comprising a first pump housing and a first impeller rotatable with the rotor about the axis in the first pump housing. The blood pump further includes a second pump stage comprising a second pump housing and a second impeller rotatable with the rotor about the axis in the second pump housing. The first pump stage is configured to have a pressure rise that decreases sharply with increasing flow; the first pump stage flow thus being primarily a function of pump speed and impeller position. The second pump stage is configured to have a pressure rise that is primarily a function of pump speed and impeller position and substantially independent of flow.

The present invention also relates to a pump including a housing that defines first and second pump housings. A rotor is supported in the housing and rotatable about an axis. The rotor includes a first impeller disposed in the first pump housing and a second impeller disposed in the second pump housing. The pump is configured such that inlet pressures acting on the first impeller move the rotor relative to the housing in a first direction along the axis and inlet pressures acting on the second impeller move the rotor relative to the housing in a second direction along the axis opposite the first direction.

The present invention also relates to a pump including a housing including a pumping chamber and a rotor supported in the housing and rotatable about an axis. The rotor includes an impeller at least partially disposed in the pumping chamber. The rotor is movable relative to the housing in an axial direction parallel to the axis. The pump is configured such that axial movement of the rotor causes the impeller to move axially between the pumping chamber and an adjacent chamber to alter the hydraulic performance of the pump.

The present invention also relates to a pump with a motor that includes a stator and a rotor. The stator is energizable to impart the rotor to rotate about an axis. The motor is configured to permit the rotor to move axially relative to the stator during operation of the pump. A first pumping stage includes a first pump housing and a first impeller positioned in the first pump housing. The first impeller is connected to a first end of the rotor and is rotatable with the rotor about the axis. The first pump housing and first impeller are configured to adjust hydraulic performance characteristics of the first pumping stage depending on the axial position of the first impeller in the first pump housing. A second pumping stage includes a second pump housing and a second impeller positioned in the second pump housing. The second impeller is connected to a second end of the rotor and is rotatable with the rotor about the axis. The second pump housing and second impeller are configured to adjust hydraulic performance characteristics of the second pumping stage depending on the axial position of the first impeller in the first pump housing. The first pumping stage is configured to urge the rotor in a first axial direction relative to the stator in response to inlet pressures acting on the first impeller, The second pumping stage is configured to urge the rotor in a second axial direction relative to the stator opposite the first axial direction in response to inlet pressures acting on the second impeller.

The present invention further relates to a total artificial heart pump that includes a left pump stage with an inlet for receiving left atrial blood flow and an outlet for discharging systemic blood flow via the aorta. The pump also includes a right pump stage with an inlet for receiving right atrial blood flow and an outlet for discharging pulmonary blood flow via the pulmonary artery. A motor includes a stator and a rotor for rotating a left impeller of the left pump stage and a right impeller of the right pump stage. The motor is configured to permit the rotor to move axially relative to the stator during operation of the pump. The pump is adapted such that differentials in left and right atrial pressures adjust the axial position of the rotor which adjusts the relative hydraulic performance characteristics of the left and right pump stages to balance the left and right atrial pressures and balance the systemic and pulmonary discharge blood flows.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 19 is a graph illustrating hydraulic performance characteristics of the blood pump of FIG. 2.

DESCRIPTION OF EMBODIMENTS

Figure 1:
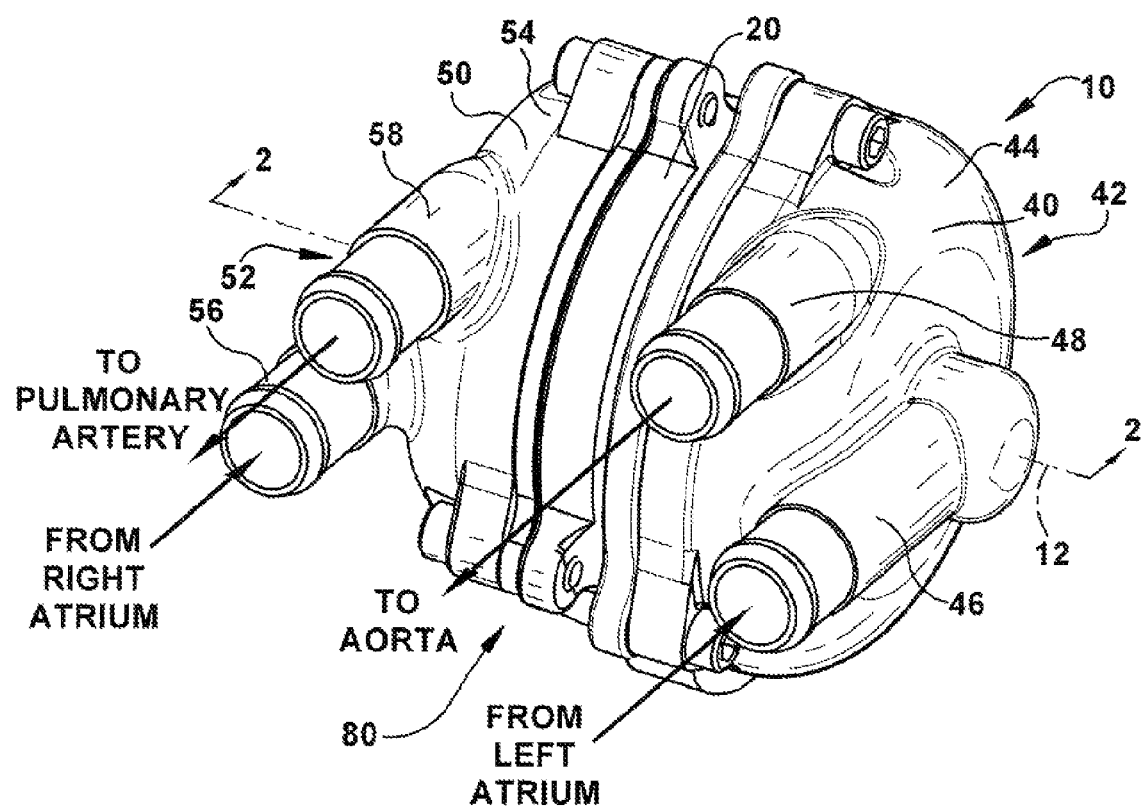
FIG. 1 is a perspective view of a blood pump according to a first embodiment of the present invention.

The present invention relates to a blood pump. FIG. 1 illustrates a blood pump 10 according to a first embodiment of the present invention. According to the present invention, the blood pump 10 is a total artificial heart (TAH) device capable of replacing a failing or damaged human heart. Those skilled in the art, however, will appreciate that the blood pump 10 could be suitable for non-TAH implementations, such as biventricular support. Those skilled in the art will also appreciate that the pump may be suited for purposes other than pumping blood, such as any implementation in which a dual or two stage fluid handling pump with pressure balancing features is desired. In the illustrated embodiments, the blood pump 10 is a two-stage centrifugal pump, which is described below in further detail. The blood pump 10 could, however, be a rotodynamic pump of any desired configuration.

Figure 2:
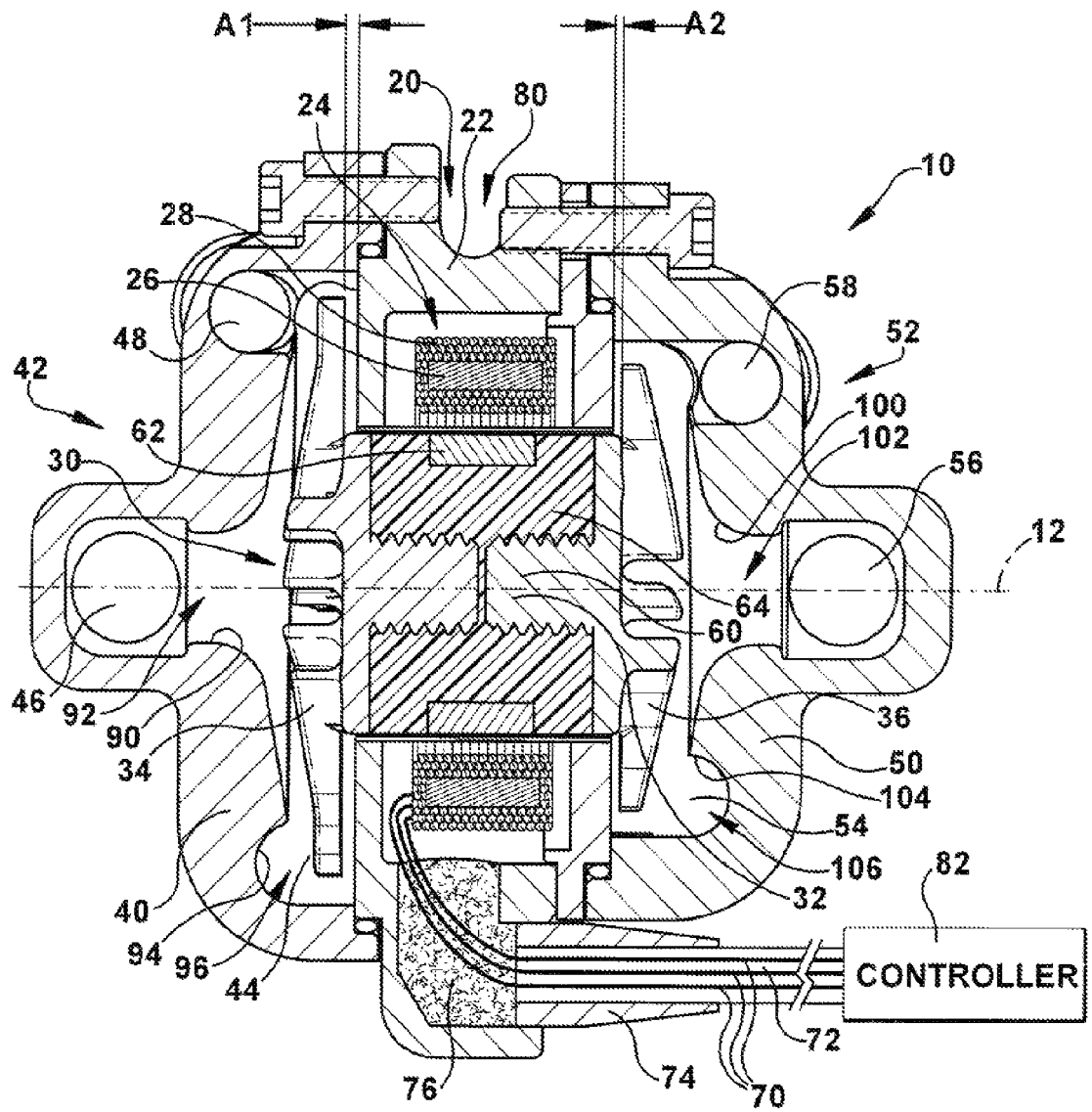
FIG. 2 is a sectional view of the blood pump taken generally along line 2-2 in FIG. 1.
Figure 3:
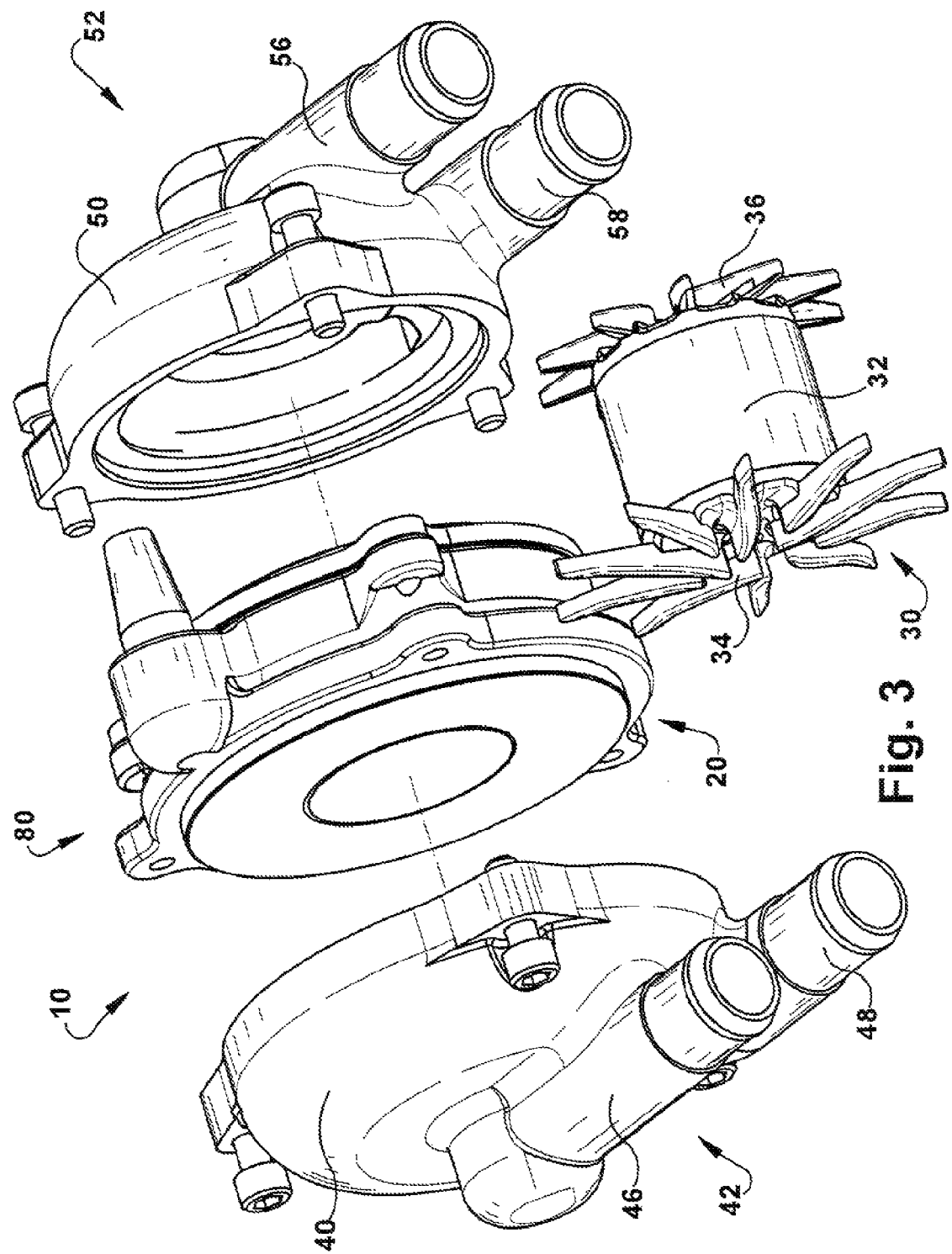
FIG. 3 is an exploded view of the blood pump of FIG. 1.

Referring to FIGS. 1-3, the blood pump 10 includes a stator assembly 20, a rotor assembly 30, a left pump housing 40, and a right pump housing 50. In an assembled condition of the blood pump 10 (FIGS. 1 and 3), the rotor assembly 30 is supported by the stator assembly 20 for rotation about an axis 12. The pump housings 40 and 50 are fixed to the stator assembly 20 to enclose the rotor assembly 30. The rotor assembly 30 includes a motor rotor 32, a first or left impeller 34, and a second or right impeller 36.

The motor rotor 32 includes a core 60 (FIG. 2) upon which a ring-shaped permanent magnet 62 is mounted. A low density magnetically permeable fill material 64 may be used to support the magnet 62 on the motor rotor 32, thereby allowing a neutral buoyancy rotating assembly, and insensitivity to pump assembly attitude. The left and right impellers 34 and 36 are secured to the core 60 by known means, such as adhesives or mechanical fasteners. Alternatively, the impellers 34 and 36 could be formed (e.g., molded) as a single piece of material with the core 60.

The stator assembly 20 includes a stator housing 22 that supports a motor stator 24. The motor stator 24 includes a stator core and motor windings, illustrated schematically at 26 and 28, respectively in FIG. 2. The motor windings 28 are electrically connected to three control wires 70 of a control cable 72 that enters the stator housing 22 through a conduit 74 and is sealed by a potting material 76.

The blood pump 10, when assembled, includes a centrifugal first or left pumping stage or pump 42. The left pump 42 includes the left impeller 34 and a left pump chamber 44 in which the left impeller is disposed. The left pump chamber 44 is defined, at least partially, by the left pump housing 40 and the stator assembly 20. The left pump 42 also includes a left pump inlet 46 and a left pump outlet 48 that, in the illustrated embodiment, are formed as integral portions of the left pump housing 40. The left pump housing 40 includes an inlet surface 90 that helps define an inlet portion 92 of the left pump chamber 44 in fluid communication with the inlet 46. The left pump housing 40 also includes a volute surface 94 that helps define a volute portion 96 of the left pump chamber 44 in fluid communication with the outlet 48.

The blood pump 10, when assembled, also includes a centrifugal second or right pumping stage or pump 52. The right pump 52 includes the right impeller 36 and a right pump chamber 54 in which the right impeller is disposed. The right pump chamber 54 is defined, at least partially, by the right pump housing 50 and the stator assembly 20. The right pump 52 also includes a right pump inlet 56 and a right pump outlet 58 that, in the illustrated embodiment, are formed as integral portions of the right pump housing 50. The right pump housing 50 includes an inlet surface 100 that helps define an inlet portion 102 of the right pump chamber 54 in fluid communication with the inlet 56. The right pump housing 50 also includes a volute surface 104 that helps define a volute portion 106 of the right pump chamber 54 in fluid communication with the outlet 58.

The motor rotor 32 and motor stator 24 help define a motor 80 of the blood pump 10 that drives the left and right pumps 42 and 52. The motor 80 may be any type of electric motor suited to drive the pumps 42 and 52 and deliver the desired performance characteristics. For example, in the illustrated embodiment, the motor 80 may have a single phase or multi-phase brushless, sensorless DC motor configuration. A motor controller 82 is operative to excite the phase windings 28 of the motor 80 via the cable 72 to achieve desired performance of the motor portion, such as motor speed or current. For example, the motor controller 82 apply pulse width modulated voltage to the motor phases in order to achieve the desired motor/pump performance.

During operation of the blood pump 10, the rotor assembly 30 rotates about the axis 12 relative to the stator assembly 20. The rotor assembly 30 is supported or rides on a hydrodynamic or fluid film bearing formed by the pumped fluid, i.e., blood. Alternatively, the blood pump 10 could include other types of bearing features, such as mechanical bearings or bearing surfaces formed from or coated with low friction materials, for facilitating rotation of the rotor assembly 30. As a further alternative, the rotor assembly 30 could be magnetically suspended.

The materials used to construct the blood pump 10 may be formed from materials conducive to blood pumping implementations. For example, portions of the blood pump 10 that are exposed to blood flow during use, such as the impellers 34 and 36 and pump housings 40 and 50, may be formed from, coated, or encased in a biocompatible material, such as stainless steel, titanium, ceramics, polymeric materials, composite materials, or a combination of these materials. Surfaces or portions of the blood pump 10 that may contact each other during use, such as the left impeller 34 and pump housing 40 or the right impeller 36 and pump housing 50, may also be formed or coated with low friction materials, such as a fluorocarbon polymer coatings, diamond-like carbon coatings, ceramics, titanium, and diamond coated titanium.

Referring to FIG. 1, arrows are used to illustrate the blood pump 10 in a total artificial heart (TAH) implementation in which the pump takes over the function of a patient's heart (not shown). In this configuration, the left pump inlet 46 is connected with the left atrium, the left pump outlet 48 is connected to the aorta, the right pump inlet 56 is connected to the right atrium, and the right pump outlet 58 is connected to the pulmonary artery. In operation, the left pump 42 delivers oxygenated blood to the aorta from the left atrium and the right pump 52 delivers deoxygenated blood to the pulmonary artery from the right atrium.

Those skilled in the art will appreciate that, in a TAH scenario, it is important to balance pulmonary and systemic arterial blood flows and atrial pressures. For example, if the right pump 52 delivers blood at a higher flow rate than the left pump 42, blood may accumulate in the lungs and can lead to congestive heart failure. For example, if the left pump 42 delivers blood at a higher flow rate than the right pump 52, blood may accumulate in the liver and can lead to liver failure. The goal for the blood pump 10 is thus to balance pulmonary and systemic arterial blood flows and atrial pressures. According to the present invention, the blood pump 10 balances systemic and pulmonary atrial pressures and arterial flow rates by adjusting the geometry or configuration of the left (systemic) pump 42 and right (pulmonary) pump 52.

According to the present invention, the blood pump 10 is configured with a clearance that permits axial movement of the rotor assembly 30 relative to the stator assembly 20. Referring to FIG. 2, the rotor assembly 30 is positioned about midpoint in this axial clearance, leaving an axial back clearance between the left impeller 34 and the stator housing 22, identified generally at "A1," and an axial back clearance between the right impeller 36 and the stator housing 22, identified generally at "A2." With the configuration shown in FIG. 2, it has been found that maximum left pump 42 performance occurs when A1 is minimum, and maximum right pump 52 performance occurs when A2 is minimum. During operation of the blood pump 10, the rotor assembly 30 can move or shuttle axially relative to the stator assembly 20 due to hydrodynamic pumping forces created by the left and right pumps 42 and 52. The rotor assembly 30 can move axially between a left position, in which the left impeller 34 is positioned with A1 being maximum, and a right position, in which the right impeller 36 is positioned with A2 being maximum.

When the rotor assembly 30 moves axially between the left and right positions, the configurations or geometries of the left and right pumps 42 and 52 are altered. As the axial position of the left impeller 34 changes, the clearance A1 between the left impeller and the stator assembly 22 changes, which alters the configuration and geometry of the left pump 42 and left pump chamber 44. Similarly, as the axial position of the right impeller 36 changes, the clearance A2 between the right impeller and the stator assembly 22 changes, which alters the configuration and geometry of the right pump chamber 54 and the configuration or geometry of the right pump 52.

As the clearances A1 and A2 increase, the first and second pumps 42 and 52 decrease in hydraulic output. Thus, for a given pump speed, as the impellers 34 and 36 move toward the stator assembly 22 (i.e., reducing their respective clearances A1 and A2), the pumps 42 and 52 increase in pressure and flow accordingly. Conversely, as the impellers 34 and 36 move away from the stator assembly 22 (i.e., increasing their respective clearances A1 and A2), the pumps 42 and 52 decrease in pressure and flow accordingly.

It will thus be appreciated that, for the single motor, two-stage configuration of the blood pump 10 of the present invention, axial movement of the rotor assembly 30 that produces increased pressure and flow at the left pump stage 42 will also produce a decrease in pressure and flow at the right pump stage 52. Similarly, axial movement of the rotor assembly 30 that produces increased pressure and flow at the right pump stage 52 will also produce a decrease in pressure and flow at the left pump stage 42. From this, it follows that, for any given speed of the blood pump 10, the pressures and flows of the left and right pump stages 42 and 52 can be balanced if the axial position of the rotor assembly 30 relative to the stator assembly 20 is adjusted to the proper position.

Based on this principle, using the blood pump 10, systemic and pulmonary pressure and flow characteristics can be controlled through adjusting the axial position of the rotor assembly 30. According to the present invention, the axial position of the of the rotor assembly 30 can be controlled passively or actively. The embodiment of FIGS. 1-5 illustrates a configuration of the blood pump 10 in which passive control is used to adjust the axial position of the rotor assembly 30 and, thus, the geometry or configuration of the left and right pumps 42 and 52.

Figure 4:
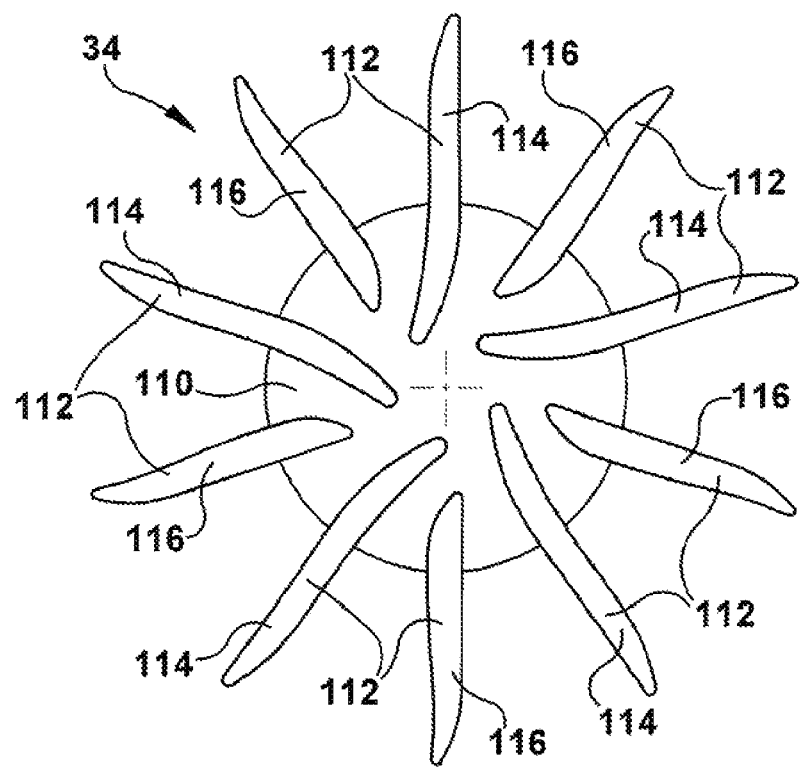
FIGS. 4 and 5 are plan views of portions of the blood pump of FIG. 1.

In the passive control configuration of the blood pump 10, the axial position of the rotor assembly 30 is controlled passively or inherently through hydraulic forces created by the left and right pumps 42 and 52 during operation. According to the present invention, the configurations of the left and right impellers 34 and 36 are chosen to help produce this operation. Referring to FIG. 4, the first impeller 34 includes a back plate 110 and a plurality of vanes 112 that extend radially from the back plate. In the embodiment of FIG. 4, the vanes 112 include first or primary vanes 114 and second or splitter vanes 116, the splitter vanes being shorter than the primary vanes. In the embodiment illustrated in FIG. 5, the vanes 112 are configured with a low incidence inlet and a radial discharge.

Figure 5:
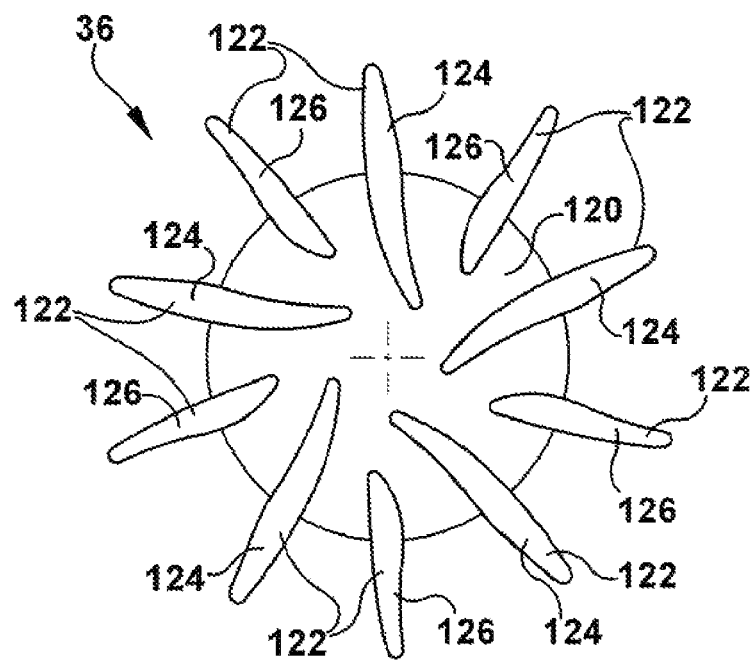

Referring to FIG. 5, the second impeller 36 includes a back plate 120 and a plurality of vanes 122 that extend radially from the back plate. In the embodiment of FIG. 5, the vanes 122 include first or primary vanes 124 and second or splitter vanes 126, the second vanes being shorter than the first vanes. In the embodiment illustrated in FIG. 5, the vanes 122 are configured with a low incidence inlet and a radial discharge.

The back plates 110 and 120 of the first and second impellers 34 and 36 are about equal in size or diameter. The vanes 112 of the first impeller 34 are longer than the corresponding vanes 122 of the second impeller 36. The configurations of the first and second impellers 34 and 36 in the embodiment of FIGS. 1-4 illustrate one example impeller configuration. Those skilled in the art will appreciate that the impellers 34 and 36 could have alternative configurations.

The back plates 110 and 120 have reduced diameters such that the vanes 112 and 122, respectively, extend radially beyond their outer edges. The back plates 110 and 120 are directly facing the left and right pump inlets 46 and 56, respectively. Therefore, fluid pressures acting on the back plates 110 and 120 are primarily inlet pressures and thus exert forces on the rotor assembly 30 that are primarily axial, i.e., parallel to the axis 12. Outlet pressures produced by the blood pump 10 are generated primarily at the end portions of the vanes 112 and 122 that are positioned radially beyond the outer diameter of the back plates 110 and 120.

The blood pump 10 of the illustrated embodiment has a configuration that differs from that of a conventional centrifugal pump design in two basic ways. First, the blood pump 10 utilizes an open-vaned impeller with an unusually high axial clearance having non-symmetrical front and back axial clearances (see FIGS. 2 and 3). Second, the radial vanes extend into the volute section in a manner typical for a peripheral (or regenerative) pump. This extension creates a back-of-vane clearance for passive performance modulation. Also, the rotor magnet 62, being shorter than the stator core 26, allows for a controlled amount of free axial movement of the rotating assembly 30.

It has been found that for constant system resistances, output flow and pump speed have a linear relationship. As a result, the control algorithm executed by the controller 82 adjusts pump speed to provide a nominal systemic flow. Balanced systemic and pulmonary flows are achieved by adjusting of the axial position of the rotor assembly 30. According to the first embodiment of the invention, the axial adjustments of the rotor assembly 30 occur inherently or automatically as a result of the configurations of the left and right impellers 34 and 36 and due to hydraulic pressures.

Because the axial hydrodynamic forces acting on the back plate portions 110 and 120 of the impellers 34 and 36 are primarily those created by pump inlet pressures, the axial position of the rotor assembly 30 adjusts in response to pressure differentials between the left and right inlet portions 92 and 102. As the axial position of the rotor assembly 30 adjusts, the geometry and hydraulic performance of the left and right pumps 42 and 52 changes, as described above. This produces a corresponding change or adjustment in the outlet flows and pressures of the left and right pumps 42 and 52, trading pressure and flow performance between the two pumps. The blood pump 10 is thus configured with a self-adjusting rotor assembly 30 that helps balance pulmonary and systemic flows, as well as atrial pressures, through incremental changes the hydraulic performance of the left and right pumps 42 and 52.

When operating in high clearance, minimum pump performance occurs when the pumping vanes are centered in the axial clearance (front and back clearances equal). Therefore, performance can be modulated by moving the impellers 34 and 36 in either axial direction. In the self-balancing configuration of FIG. 2, maximum performance for the left pump 42 occurs when back clearance A1 is minimum, while maximum performance for the right pump 52 occurs when back clearance A2 is minimum. The passive control implemented in the embodiment of FIG. 2 modulates performance by adjusting the back clearances A1 and A2. The advantage of using the back (inside) edges to modulate performance is that hydraulic forces operating on the rotating assembly can enforce the correct direction of axial movement for passive control, thereby eliminating the need for an active axial control system.

During operation of the blood pump 10 as TAH, pump speed can be modulated at normal pulse rates to create pulsatile flow and pressure, simulating normal hemodynamics in the patient. For example, it was found that a ±30% speed modulation enforces a highly pulsatile condition. Further, the speed wave form can be adjusted to tailor the characteristics of the systemic pressure pulses to mimic the amplitude and systolic/diastolic timing desired clinically.

Advantageously, since flow is directly related to current and speed, the current wave form can be analyzed to determine any interruptions in flow during each control cycle. This may, for example, help detect collapse of the left or right atria, in which case an incremental decrease in average speed or magnitude of the speed pulsation may be triggered automatically. Also, based on the motor current response to the speed and duty cycle, the patient's pulmonary and systemic pressures and vascular resistances can be estimated by calculation, allowing the system to be used as a continuous patient monitor.

Figure 6:
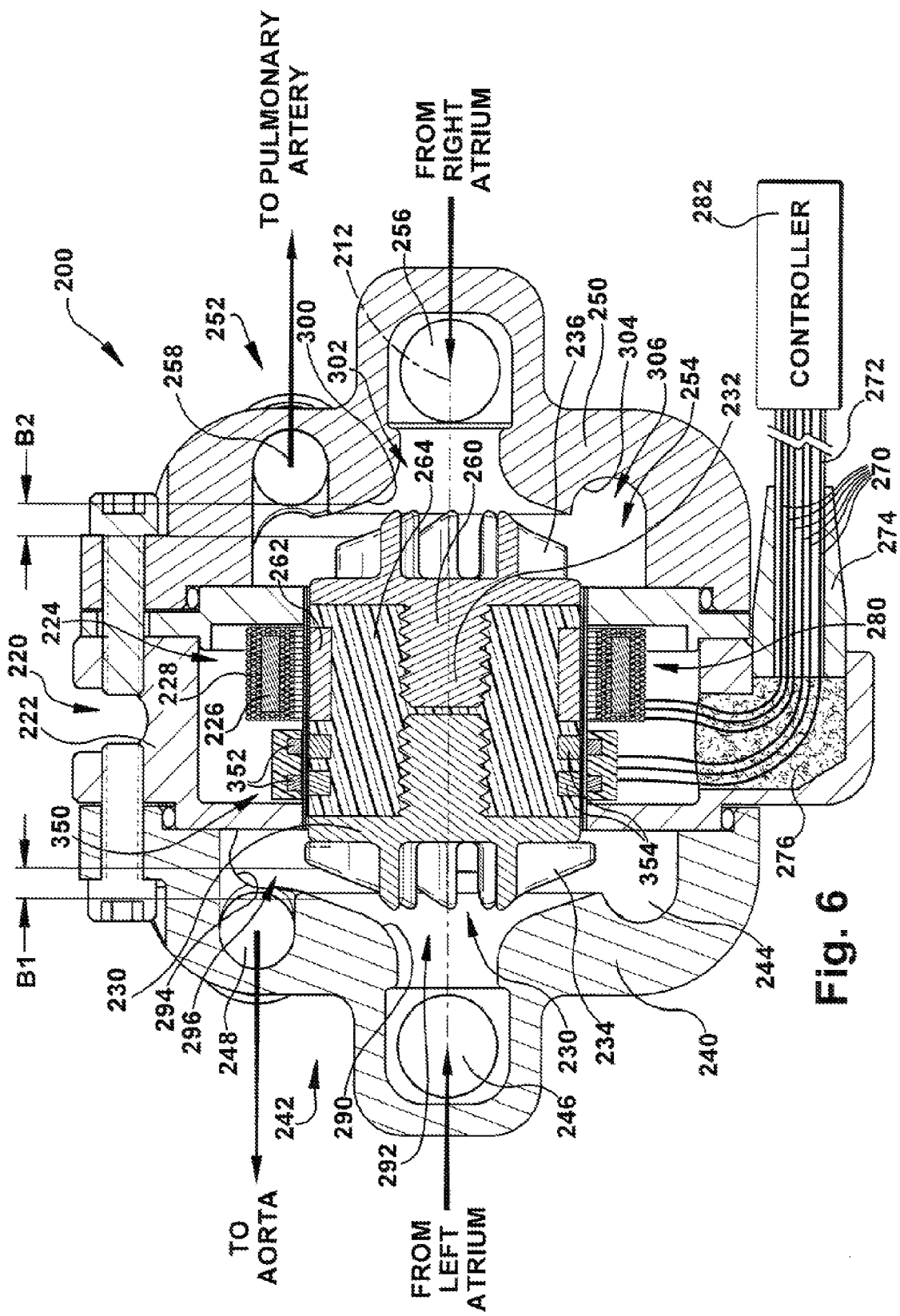
FIG. 6 is a sectional view illustrating a blood pump according to a second embodiment of the present invention.

A second embodiment of the present invention is illustrated in FIG. 6. The second embodiment of the invention is similar to the first embodiment of the invention illustrated in FIGS. 1-5. Referring to FIG. 6, the blood pump 200 has a two-stage centrifugal pump configuration similar to that of FIGS. 1-5. The blood pump 200 may thus be configured for use as a total artificial heart (TAH) device. The blood pump 200 could, however, be suitable for non-TAH implementations, such as biventricular support or any implementation in which a dual or two stage fluid handling pump with pressure balancing features is desired.

Referring to FIG. 6, the blood pump 200 includes a stator assembly 220, a rotor assembly 230, a left pump housing 240, and a right pump housing 250. In the assembled condition, the rotor assembly 230 is supported by the stator assembly 220 for rotation about an axis 212. The pump housings 240 and 250 are fixed to the stator assembly 220 to enclose the rotor assembly 230. The rotor assembly 230 includes a motor rotor 232, a first or left impeller 234, and a second or right impeller 236.

The motor rotor 232 includes a core 260 upon which a ring-shaped permanent motor magnet 262 is mounted. A fill material 264, such as a low density magnetically permeable material, may be used to help support the magnet 262 on the motor rotor 232. The left and right impellers 234 and 236 are secured to the core 260 by known means, such as adhesives or mechanical fasteners. Alternatively, the impellers 234 and 236 could be formed (e.g., molded) as a single piece of material with the core 260.

The stator assembly 220 includes a stator housing 222 that supports a motor stator 224. The motor stator 224 includes a stator core and motor windings, illustrated schematically at 226 and 228, respectively in FIG. 6. The motor windings 228 are electrically connected to control wires 270 of a control cable 272 that enters the stator housing 222 through a conduit 274 and is sealed by a potting material 276.

The blood pump 200, when assembled, includes a centrifugal first or left pumping stage or pump 242. The left pump 242 includes the left impeller 234 and a left pump chamber 244 in which the left impeller is disposed. The left pump chamber 244 is defined, at least partially, by the left pump housing 240 and the stator assembly 220. The left pump 242 also includes a left pump inlet 246 and a left pump outlet 248 that, in the illustrated embodiment, are formed as integral portions of the left pump housing 240. The left pump housing 240 includes an inlet surface 290 that helps define an inlet portion 292 of the left pump chamber 244 in fluid communication with the inlet 246. The left pump housing 240 also includes a volute surface 294 that helps define a volute portion 296 of the left pump chamber 244 in fluid communication with the outlet 248.

The blood pump 200, when assembled, also includes a centrifugal second or right pumping stage or pump 252. The right pump 252 includes the right impeller 236 and a right pump chamber 254 in which the right impeller is disposed. The right pump chamber 254 is defined, at least partially, by the right pump housing 250 and the stator assembly 220. The right pump 252 also includes a right pump inlet 256 and a right pump outlet 258 that, in the illustrated embodiment, are formed as integral portions of the right pump housing 250. The right pump housing 250 includes an inlet surface 300 that helps define an inlet portion 302 of the right pump chamber 254 in fluid communication with the inlet 256. The right pump housing 250 also includes a volute surface 304 that helps define a volute portion 306 of the right pump chamber 254 in fluid communication with the outlet 258.

The motor rotor 232 and motor stator 224 help define a motor 280 of the blood pump 200 that drives the left and right pumps 242 and 252. The motor 280 may be any type of electric motor suited to drive the pumps 242 and 252 and deliver the desired performance characteristics. For example, in the illustrated embodiment, the motor 280 may have a multi-phase brushless DC motor configuration. A motor controller 282 is operative to excite the phase windings 228 of the motor 280 via the cable 272 to achieve desired performance of the motor portion, such as motor speed or current. For example, the motor controller 282 apply pulse width modulated voltage to the motor phases in order to achieve the desired the desired motor/pump performance.

During operation of the blood pump 200, the rotor assembly 230 rotates about the axis 212 relative to the stator assembly 220. The rotor assembly 230 is supported or rides on a hydrodynamic or fluid film bearing formed by the pumped fluid, i.e., blood. Alternatively, the blood pump 200 could include other types of bearing features, such as mechanical bearings or bearing surfaces formed from or coated with low friction materials, for facilitating rotation of the rotor assembly 230. As a further alternative, the rotor assembly 230 could be magnetically suspended.

The materials used to construct the blood pump 200 may be formed from materials conducive to blood pumping implementations. For example, portions of the blood pump 200 that are exposed to blood flow during use, such as the impellers 234 and 236 and pump housings 240 and 250, may be formed from, coated, or encased in a biocompatible material, such as stainless steel, titanium, ceramics, polymeric materials, composite materials, or a combination of these materials. Surfaces or portions of the blood pump 200 that may contact each other during use, such as the left impeller 234 and pump housing 240 or the right impeller 236 and pump housing 250, may also be formed or coated with low friction materials, such as fluorocarbon polymer coatings, diamond-like carbon coatings, ceramics, titanium, and diamond coated titanium.

In FIG. 6, arrows are used to illustrate the blood pump 200 in a total artificial heart (TAH) implementation in which the pump takes over the function of a patient's heart (not shown). In this configuration, the left pump inlet 246 is connected with the left atrium, the left pump outlet 248 is connected to the aorta, the right pump inlet 256 is connected to the right atrium, and the right pump outlet 258 is connected to the pulmonary artery. In operation, the left pump 242 delivers oxygenated blood to the aorta from the left atrium and the right pump 252 delivers deoxygenated blood to the pulmonary artery from the right atrium.

According to the present invention, the blood pump 200 balances systemic and pulmonary pressures and flow rates by adjusting the geometry or configuration of the left (systemic) pump 242 and right (pulmonary) pump 252. The blood pump 200 is configured with a clearance that permits axial movement of the rotor assembly 230 relative to the stator assembly 220. In FIG. 6, the rotor assembly 230 is positioned about midpoint in this axial clearance, leaving an axial clearance between the left impeller 234 and the left pump housing 240, identified generally at "B1," and an axial clearance between the right impeller 236 and the right pump housing 250, identified generally at "B2." During operation of the blood pump 200, the rotor assembly 230 can move or shuttle axially relative to the stator assembly 220 due to electromotive force of an actuator 350, such as an electric solenoid, that is connected to the controller 282 via the cable 272. The rotor assembly 230 can move axially between a left position, in which the left impeller 234 is positioned adjacent or engaging the left pump housing 240, and a right position, in which the right impeller 236 is positioned adjacent to the right pump housing 250.

When the rotor assembly 230 moves axially between the left and right positions, the configurations or geometries of the left and right pumps 242 and 252 are altered. As the axial position of the left impeller 234 changes, the clearance B1 between the left impeller and the left pump housing 240 changes, which alters the volume of the left pump chamber 244 and the configuration or geometry of the left pump 242. Similarly, as the axial position of the right impeller 236 changes, the clearance B2 between the right impeller and the right pump housing 250 changes, which alters the volume of the right pump chamber 254 and the configuration or geometry of the right pump 252.

As the clearances B1 and B2 increase, the first and second pumps 242 and 252 reduce hydraulic output. Thus, for a given pump speed, as the impellers 234 and 236 move toward their respective pump housings 240 and 250 (i.e., reducing their respective clearances B1 and B2), the pumps 242 and 252 increase pressure and flow increase accordingly. Conversely, as the impellers 234 and 236 move away from their respective pump housings 240 and 250 (i.e., increasing their respective clearances B1 and B2), the pumps 242 and 252 decrease pressure and flow decrease accordingly.

It will thus be appreciated that, for the single motor, two-stage configuration of the blood pump 200 of the present invention, axial movement of the rotor assembly 230 that produces increased pressure and flow at the left pump stage 242 will also produce a decrease in pressure and flow at the right pump stage 252. Similarly, axial movement of the rotor assembly 230 that produces increased pressure and flow at the right pump stage 252 will also produce a decrease in pressure and flow at the left pump stage 242. From this, it follows that, for any given speed of the blood pump 200, the pressures and flows of the left and right pump stages 242 and 252 can be balanced if the axial position of the rotor assembly 230 relative to the stator assembly 220 is adjusted to the proper position.

Based on this principle, using the blood pump 200, systemic and pulmonary pressure and flow characteristics can be controlled through adjusting the axial position of the rotor assembly 230. According to the second embodiment of the present invention, the blood pump 200 is configured for active control of the axial position of the of the rotor assembly 230 and, thus, the geometry or configuration of the left and right pumps 242 and 252.

It has been found that, for constant system resistances, output flow and pump speed have a linear relationship. It has also been found that, for a given pump speed, there is an electrical power level, obtained by adjusting the axial position of the rotor assembly 230, that corresponds with balanced flows at the left pump 242 and right pump 252. As a result, the control algorithm executed by the controller 282 adjusts pump speed to provide a nominal systemic flow, while balanced systemic and pulmonary flows are achieved by adjusting of the axial position of the rotor assembly 230. According to the second embodiment of the invention, the axial adjustments of the rotor assembly 230 relative to the stator assembly 220 are achieved through the use of an electro-mechanical actuator 350, such as a solenoid, that is connected to the controller 282 via the cable 272. The solenoid 350 is actuatable to one of two positions: a first or left position and a second or right position. In the left position, the solenoid 350 causes the axial position of the rotor assembly 230 to shift to a first or left position, in which the left impeller 234 is positioned adjacent or near the inlet surface 290 of the left pump housing 240, effectively increasing the hydraulic output of the left pump stage 242 and decreasing the hydraulic output of the right pump stage 252, as described above. In the right position, the solenoid 350 causes the axial position of the rotor assembly 230 to shift to a second or right position, in which the right impeller 236 is positioned adjacent or near the inlet surface 300 of the right pump housing 250, effectively increasing the hydraulic output of the right pump stage 252 and decreasing the hydraulic output of the left pump stage 252, as described above.

The solenoid 350 may be configured to place the rotor assembly 230 in the left and right positions in a variety of manners. For example, the solenoid 350 may be a latching solenoid. In this configuration, the solenoid 350 may include two separate coils 352, one for selecting the left position and one for selecting the right position, fixed to the stator assembly 220 and an armature 354, such as one or more magnets, fixed to the rotor assembly 230. In this latching configuration, the solenoid 350 includes a magnetic latching mechanism that maintains the rotor assembly 230 in the selected position without constant application of power to the solenoid. In operation, the coils 352 may be energized by a short current pulse of sufficient magnitude and duration to move the armature 354, and thus the rotor assembly 230, to the desired left/right position. At this point, the latching mechanism is actuated and maintains the rotor 230 at the desired position. When the opposite coil is energized, the latching mechanism releases the rotor assembly 230 to move to the opposite position under the pull of the coil 352 on the armature 354. The mechanism then latches magnetically, thus maintaining the axial position of the rotor assembly 230 when the coil 352 is de-energized.

In an alternative configuration, the solenoid 350 may be a ratcheting or toggle-type latching solenoid configured for pulse-left/pulse-right operation. In this configuration, the solenoid 350 may include a single coil and latch mechanism that, when the coil is energized, latches the rotor assembly alternately in the left and right positions. Thus, during operation, if the rotor assembly is in the right position, the next energy pulse will place the rotor assembly in the left position. The next energy pulse will then place the rotor assembly in the right position, and so on.

In another alternative configuration, the solenoid 350 may be a non-latching, continuous current solenoid. In this configuration, the solenoid may include a single coil for moving an armature that is spring biased to one of the left and right positions. When the coil is de-energized, the spring maintains the armature and thus the rotor, at one of the left and right positions. When the coil is energized, the armature and rotor are moved against the spring bias to the opposite position. The armature and rotor are maintained at this position until the coil is de-energized, at which time the spring moves the armature and rotor back to the original position.

In operation of the blood pump 200, motor speed is modulated at normal pulse rates to create pulsatile flow and pressure. Balanced systemic and pulmonary flow and atrial pressure balance are achieved through active adjustments of the axial position of the rotor assembly 230 via the solenoid 350 to adjust the hydraulic performance of the left and right pumps 242 and 252. These balanced flows and pressures are achieved by splitting the control cycle (e.g., 10 seconds) between the left and right positions. Left and right flow will be estimated from the speed, power consumption, and the change in power consumption as the rotor assembly 230 toggles between the left and right axial positions.

In operation, the axial position of the rotor assembly 230 is toggled back and forth between the left and right positions during the control cycle (e.g., ten seconds) of the pump 200. As the axial position of the rotor assembly 230 toggles, the geometry and hydraulic performance of the left and right pumps 242 and 252 changes, as described above. This produces a corresponding net change or adjustment in the outlet flows and pressures of the left and right pumps 242 and 252, increasing the outlet flow and pressure on one side of the pump and decreasing the outlet flow and pressure at the opposing side of the pump. The blood pump 200 and the controller 282 are thus configured to balance pulmonary and systemic flows, as well as atrial pressures, through incremental changes in the hydraulic performance of the left and right pumps 242 and 252.

The active control embodiment of the blood pump 200 of FIG. 6 uses front vane clearance to modulate performance. This has two potential advantages. First, right/left performance bias can be controlled externally at the expense of more complexity. Second, the total axial clearance is less, allowing better pump efficiency. Also, the rotor magnet 262 is shorter than the stator core 226 to allow a controlled amount of free axial movement of the rotating assembly 230.

During operation of the blood pump 200, left and right atrial pressures equilibrate to within several mmHg. As the flow approaches equilibrium, trending in the current draw of the pump 200 indicates the direction of adjustment for fine-tuning the duty cycle. Also, pump speed can be modulated at normal pulse rates to create pulsatile flow and pressure and stable hemodynamics in the patient. For example, it was found that a ±30% speed modulation enforces a highly pulsatile condition. Further, the speed wave form can be adjusted to tailor the characteristics of the systemic pressure pulses to mimic the amplitude and systolic/diastolic timing desired clinically.

Advantageously, since flow is approximately related to current, and speed, the current wave form can be analyzed to determine any interruptions in flow during each control cycle. This may, for example, help detect collapse of the left or right atria, in which case an incremental decrease in average speed or magnitude of the speed pulsation may be triggered automatically. Also, based on the speed and duty cycle, the patient's pulmonary and systemic pressures and vascular resistances can be estimated by calculation, allowing the system to be used as a continuous patient monitor.

Figure 7:
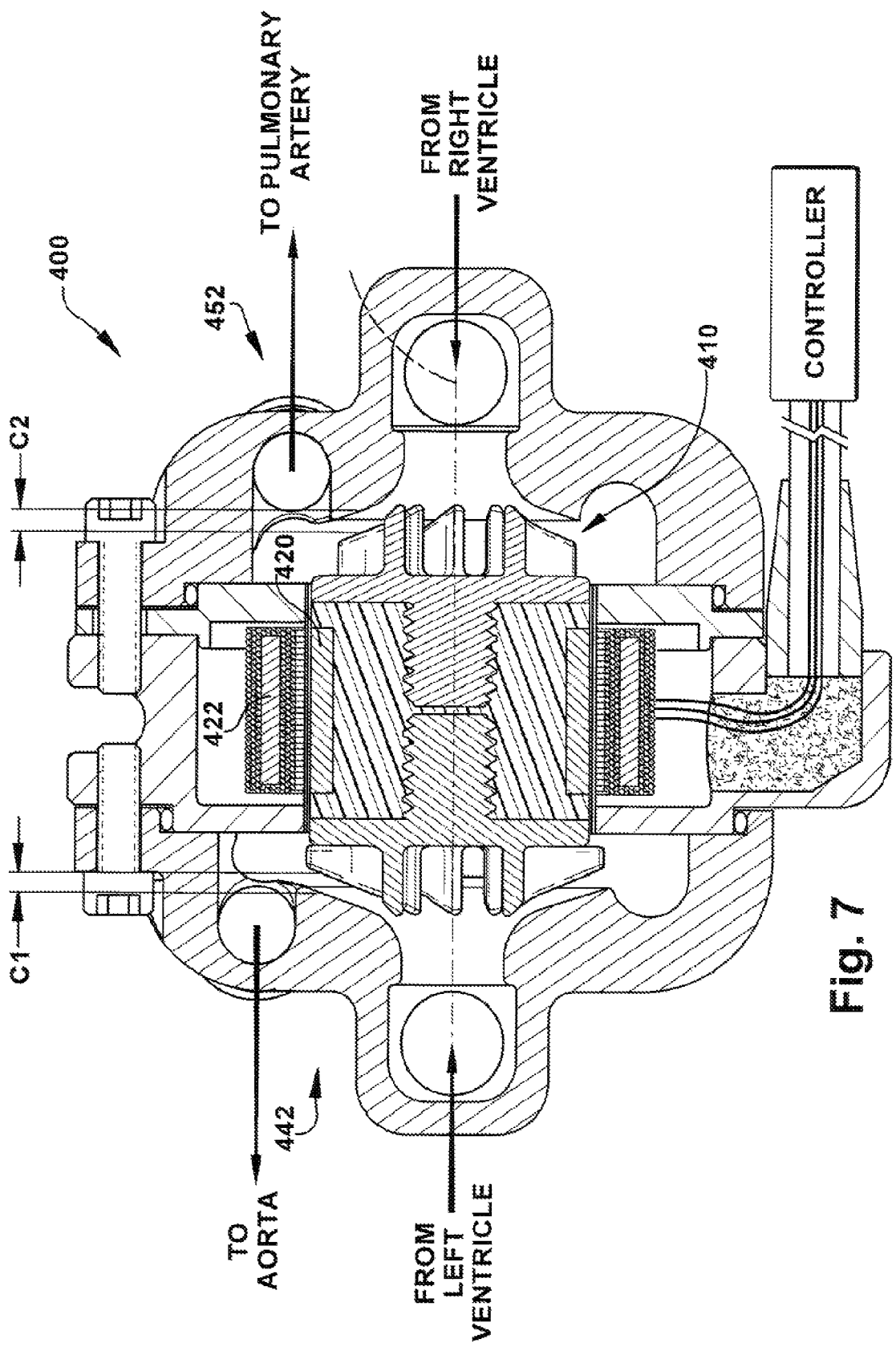
FIG. 7 is a sectional view illustrating a blood pump according to a third embodiment of the present invention.

A blood pump 400 according to a third embodiment of the present invention is illustrated in FIG. 7. The blood pump 400 of FIG. 7 has a configuration that is similar to the embodiment of FIG. 6, except that the embodiment of FIG. 7 includes a rotor assembly 410 that does not move axially to alter the pump geometry during operation. In this configuration, the rotor magnet 420 is the same length or longer than the stator core 422, which magnetically constrains the axial position of the rotor assembly 410.

Figure 8:
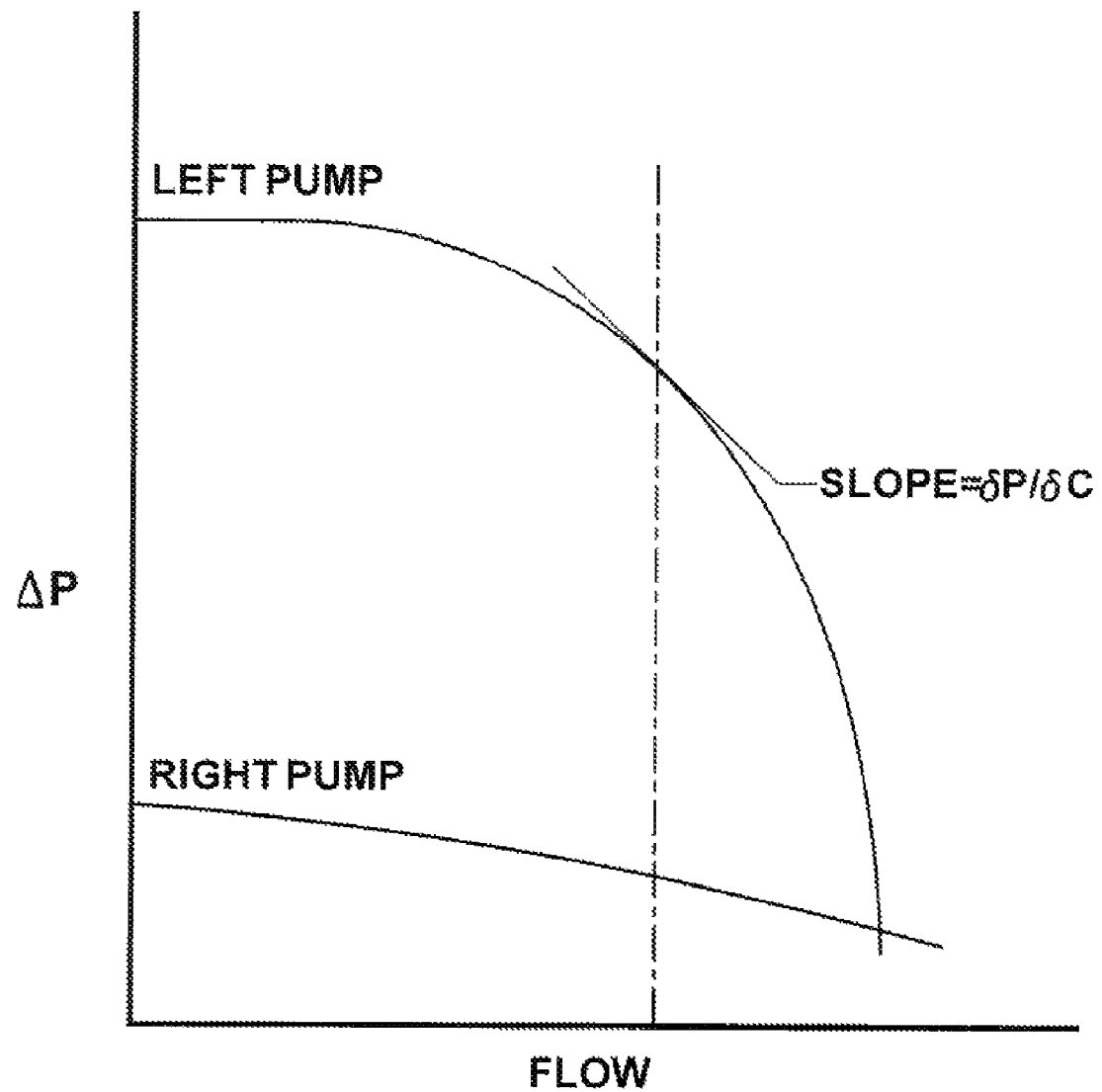
FIG. 8 is a graph illustrating performance characteristics of the blood pump of FIG. 7.

The blood pump 400 of FIG. 7 may be particularly well-suited for use as a ventricular assist device (VAD), such as a bi-ventricular assist device (BiVAD) that combines right ventricular assist device (RVAD) and left ventricular assist device (LVAD) functions in a single pump. With an RVAD, the total pulmonary artery flow is shared between the VAD and native ventricle, so precise right/left pump control is not as critical as for a total artificial heart. It has been found that performance characteristics can be crafted into the pumping element design, which can allow a degree of completely passive regulation of a BiVAD system. In this embodiment, the configurations and geometries of the left pump 442 (LVAD) and right pump 452 (RVAD) may be designed to have pressure versus flow characteristics similar to those shown in FIG. 8. As shown in FIG. 8, the left pump 442 has a pressure rise that decreases sharply with increasing flow, causing the left flow to be primarily a function of speed. The right pump 452 has a characteristic pressure rise that is a function of speed, and relatively independent of flow. In this way, the left pump 442 acts as a flow regulator for systemic flow, while the right pump 452 acts as a differential pressure regulator for moderate unloading the right ventricle.

A blood pump 500 according to a fourth embodiment of the present invention is illustrated in FIGS. 9-12. The blood pump 500 of FIGS. 9-12 has a two-stage or dual centrifugal pump configuration that is similar to the embodiments of FIGS. 1-5 and 7. The blood pump 500 may thus be configured for use as a total artificial heart (TAH) device. The blood pump 500 could, however, be suitable for non-TAH implementations, such as biventricular support or any implementation in which a dual or two stage fluid handling pump with pressure balancing features is desired.

Figure 9:
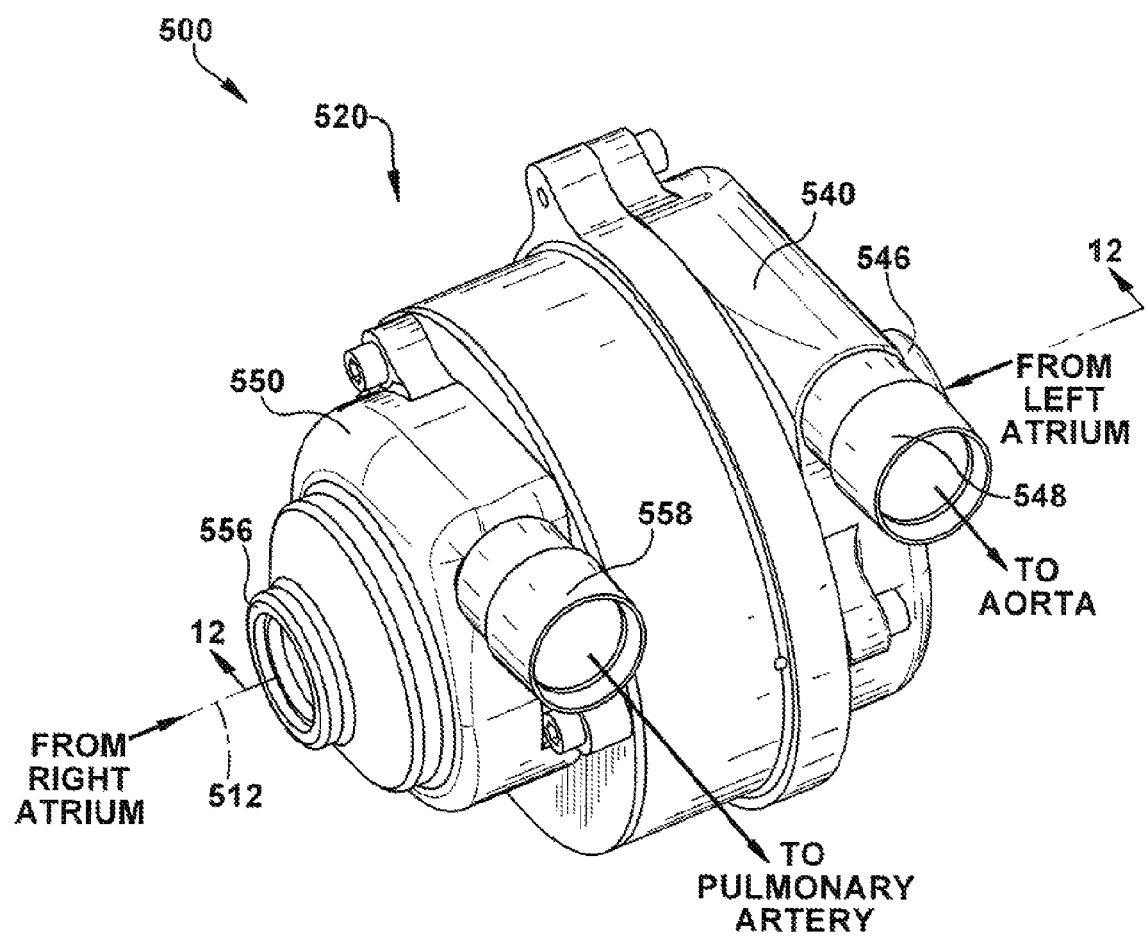
FIG. 9 is a perspective view of a blood pump according to a fourth embodiment of the present invention.
Figure 10:
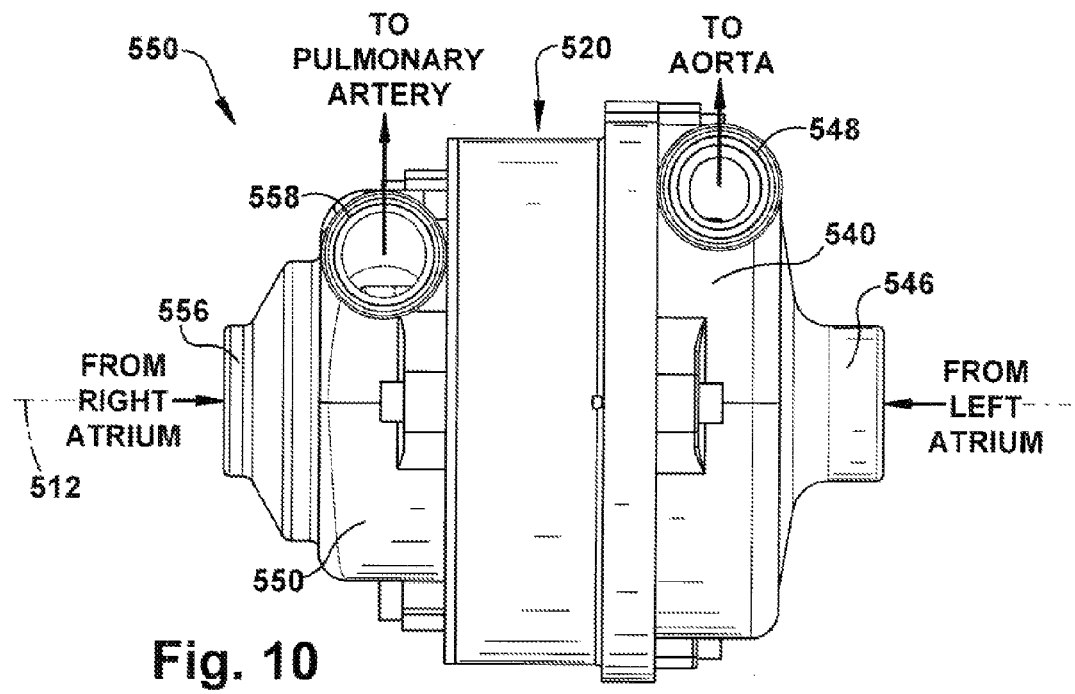
FIG. 10 is a front view of the blood pump of FIG. 9.
Figure 11:
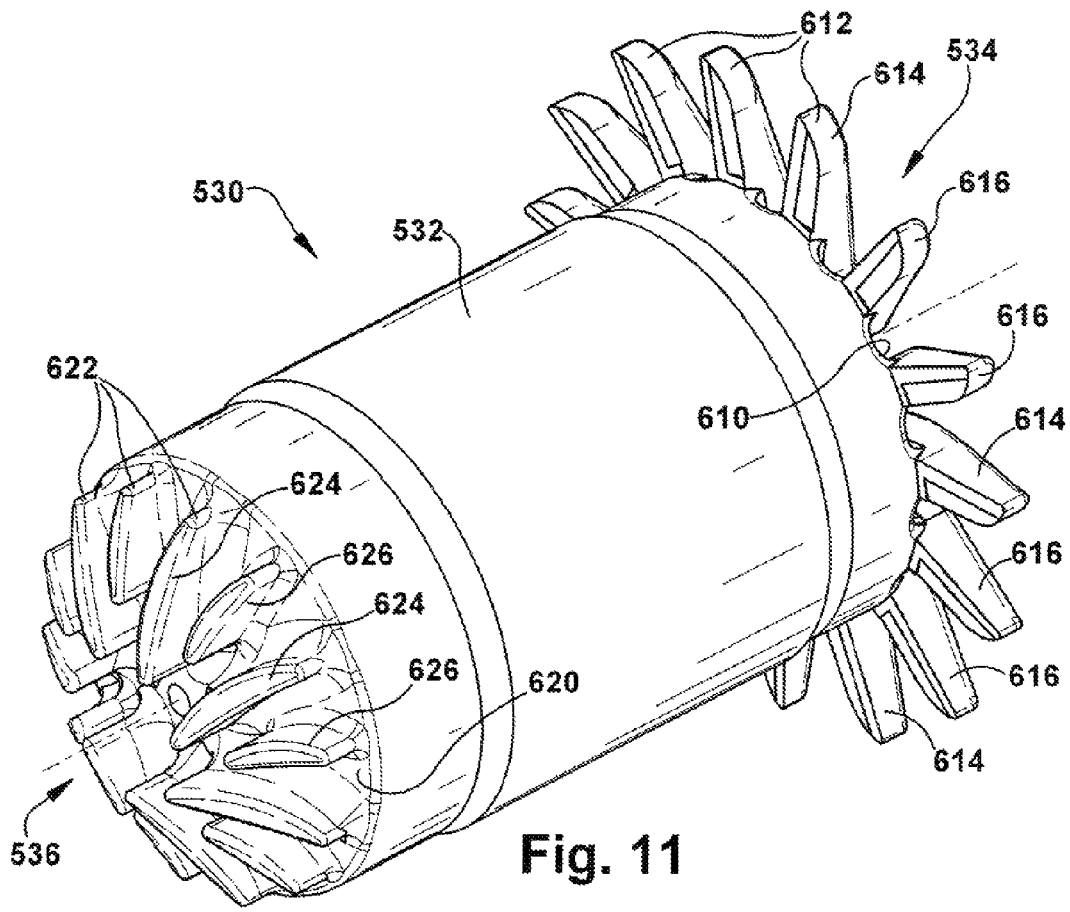
FIG. 11 is a perspective view of a portion of the blood pump of FIG. 9.

Referring to FIGS. 9-11, the blood pump 500 includes a stator assembly 520, a rotor assembly 530, a left pump housing 540, and a right pump housing 550. In an assembled condition of the blood pump 500, the rotor assembly 530 is supported by the stator assembly 520 for rotation about an axis 512. The pump housings 540 and 550 are fixed to the stator assembly 520 to enclose the rotor assembly 530. The rotor assembly 530 includes a motor rotor 532, a first or left impeller 534, and a second or right impeller 536.

The motor rotor 532 includes a core 560 (FIG. 12) surrounded or otherwise encased in a shell or casing 564 upon which a ring-shaped permanent magnet 562 is mounted. The core 560 may be constructed of a low density magnetically permeable material, may be used to help support the magnet 562 on the motor rotor 532, thereby allowing a neutral buoyancy rotating assembly and insensitivity to the attitude of the pump assembly. The left and right impellers 534 and 536 may be secured to the core 560 by known means, such as adhesives or mechanical fasteners, or, as shown in FIGS. 9-11, could be formed (e.g., molded) as a single piece of material with the shell 564.

The stator assembly 520 includes a stator housing 522 that supports a motor stator 524. The motor stator 524 includes a stator core and motor windings, illustrated schematically at 526 and 528, respectively in FIG. 12. The motor windings 528 are electrically connected to control wires 570 of a control cable 572 that enters the stator housing 522 through a conduit 574 and a strain relief material 576.

The blood pump 500, when assembled, includes a centrifugal first or left pumping stage or pump 542. The left pump 542 includes the left impeller 534 and a left pump chamber 544 in which the left impeller is disposed. The left pump chamber 544 is defined, at least partially, by the left pump housing 540 and the stator assembly 520. The left pump 542 also includes a left pump inlet 546 and a left pump outlet 548 that, in the illustrated embodiment, are formed as integral portions of the left pump housing 540. The left pump housing 540 includes an inlet surface 590 that helps define an inlet portion 592 of the left pump chamber 544 in fluid communication with the inlet 546. The left pump housing 540 also includes a volute surface 594 that helps define a volute portion 596 of the left pump chamber 544 in fluid communication with the outlet 548.

The blood pump 500, when assembled, also includes a centrifugal second or right pumping stage or pump 552. The right pump 552 includes the right impeller 536 and a right pump chamber 554 in which the right impeller is disposed. The right pump chamber 554 is defined, at least partially, by the right pump housing 550 and the stator assembly 520. The right pump 552 also includes a right pump inlet 556 and a right pump outlet 558 that, in the illustrated embodiment, are formed as integral portions of the right pump housing 550. The right pump housing 550 includes an inlet surface 600 that helps define an inlet portion 602 of the right pump chamber 554 in fluid communication with the inlet 556. The right pump housing 550 also includes a volute surface 604 that helps define a volute portion 606 of the right pump chamber 554 in fluid communication with the outlet 558. The right pump housing 550 further includes a chamber 608 adjacent the volute portion 606 into which the right impeller 536 enters as the rotor assembly 530 moves axially to the right as viewed in FIG. 12. The right impeller 536 leaves the volute portion 606 as it enters the chamber 608.

The motor rotor 532 and motor stator 524 help define a motor 580 of the blood pump 500 that drives the left and right pumps 542 and 552. The motor 580 may be any type of electric motor suited to drive the pumps 542 and 552 and deliver the desired performance characteristics. For example, in the illustrated embodiment, the motor 580 may have a single phase or multi-phase brushless, sensorless DC motor configuration. A motor controller (not shown) is operative to excite the phase windings 528 of the motor 580 via the cable 572 to achieve desired performance of the motor portion, such as motor speed or current. For example, the motor controller may apply pulse width modulated voltage to the motor phases in order to achieve the desired motor/pump performance.

Referring to FIG. 11, the first impeller 534 includes a back plate 610 and a plurality of vanes 612 that extend radially from the rotor 530. The vanes 612 include first or primary vanes 614 and second or splitter vanes 616, the splitter vanes being shorter than the primary vanes. In the embodiment illustrated in FIGS. 9-12, there are two splitter vanes 616 positioned between pairs of primary vanes 614. The vanes 612 are configured with a low incidence inlet and a radial discharge.

The second impeller 536 includes a back plate 620 and a plurality of vanes 622 that extend radially along the end face of the rotor 530. The vanes 622 include first or primary vanes 624 and second or splitter vanes 626, the second vanes being shorter than the first vanes. In the embodiment illustrated in FIGS. 9-12, the primary vanes 624 and splitter vanes 626 are arranged in an alternating fashion about the rotor 530. The vanes 622 are configured with a low incidence inlet and a radial discharge.

The vanes 612 of the first impeller 534 are longer than the corresponding vanes 622 of the second impeller 536. The configurations of the first and second impellers 534 and 536 in the embodiment of FIGS. 9-12 illustrate one example impeller configuration. Those skilled in the art will appreciate that the impellers 534 and 536 could have alternative configurations.

The back plates 610 and 620 are aligned axially with the left and right pump inlets 546 and 556, respectively. Therefore, fluid pressures acting on the back plates 610 and 620 are primarily inlet pressures and thus exert forces on the rotor assembly 530 that are primarily axial, i.e., parallel to the axis 512. Outlet pressures produced by the blood pump 500 are generated primarily at the end portions of the vanes 612 and 622. The vanes 612 of the first impeller 534 extend radially beyond the outer diameter of the back plate 610.

During operation of the blood pump 500, the rotor assembly 530 rotates about the axis 512 relative to the stator assembly 520. The rotor assembly 530 is supported or rides on a hydrodynamic or fluid film bearing formed by the pumped fluid, i.e., blood. Alternatively, the blood pump 500 could include other types of bearing features, such as mechanical bearings or bearing surfaces formed from or coated with low friction materials, for facilitating rotation of the rotor assembly 530. As a further alternative, the rotor assembly 530 could be magnetically suspended.

The materials used to construct the blood pump 500 may be formed from materials conducive to blood pumping implementations. For example, portions of the blood pump 500 that are exposed to blood flow during use, such as the impellers 534 and 536 and pump housings 540 and 550, may be formed from, coated, or encased in a biocompatible material, such as stainless steel, titanium, ceramics, polymeric materials, composite materials, or a combination of these materials. Surfaces or portions of the blood pump 500 that may contact each other during use, such as the left impeller 534 and pump housing 540, the right impeller 536 and pump housing 550, or the rotor casing 564, may also be formed or coated with low friction materials, such as a fluorocarbon polymer coatings, diamond-like carbon coatings, ceramics, titanium, and diamond coated titanium.

Those skilled in the art will appreciate that, in a TAH scenario, it is important to balance pulmonary and systemic arterial blood flows and atrial pressures. For example, if the right pump 552 delivers blood at a higher flow rate than the left pump 542, blood may accumulate in the lungs and can lead to congestive heart failure. As another example, if the left pump 542 delivers blood at a higher flow rate than the right pump 552, blood may accumulate in the liver and can lead to liver failure. The goal for the blood pump 500 is thus to balance pulmonary and systemic arterial blood flows and atrial pressures. According to the present invention, the blood pump 500 balances systemic and pulmonary atrial pressures and arterial flow rates by adjusting the geometry or configuration of the left (systemic) pump 542 and right (pulmonary) pump 552.

Figure 12:
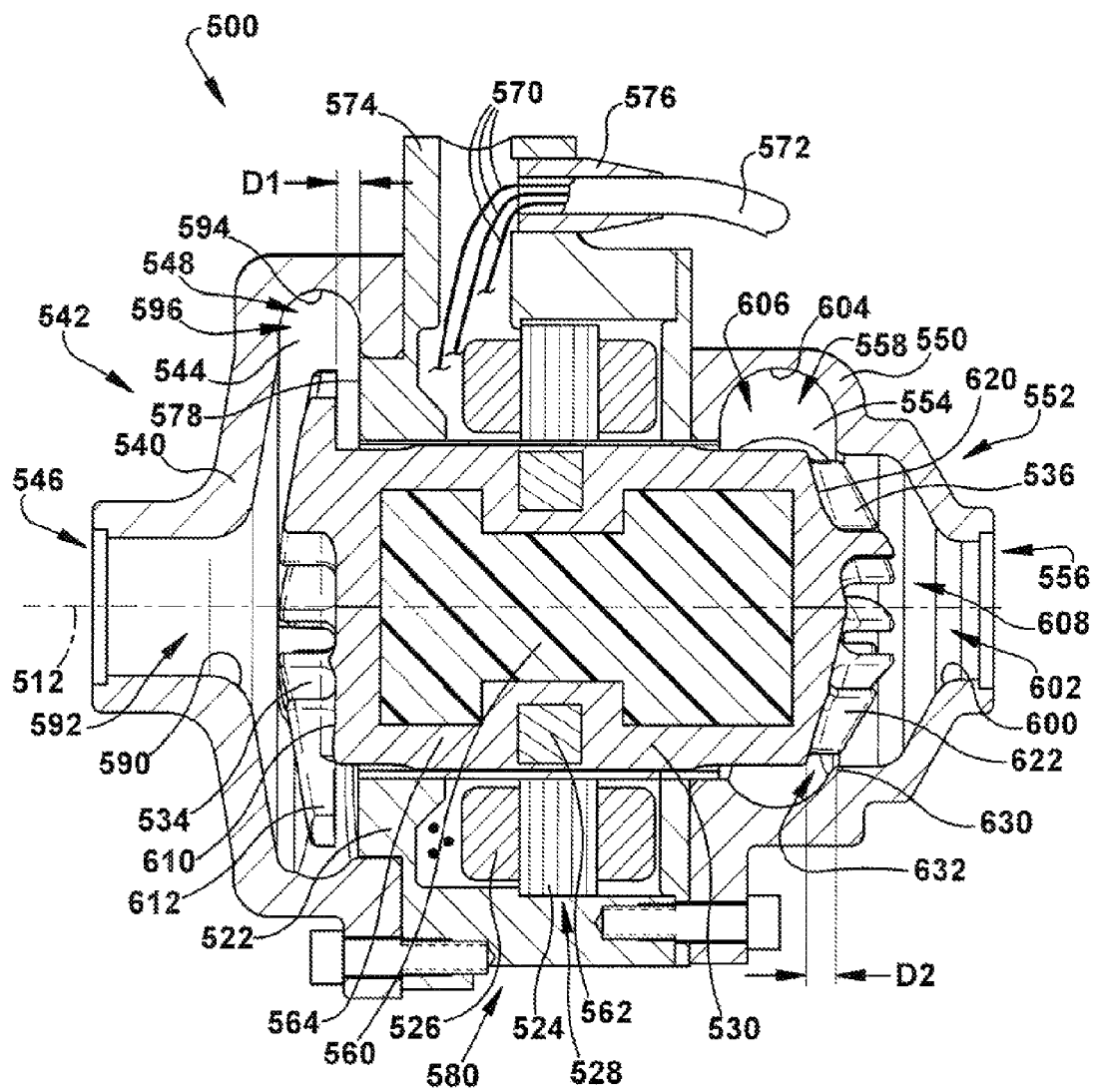
FIG. 12 is a sectional view of the blood pump taken generally along line 12-12 in FIG. 9.

According to the present invention, the blood pump 500 is configured with a clearance that permits axial movement of the rotor assembly 530 relative to the stator assembly 520. Referring to FIG. 12, the rotor assembly 530 is positioned about midpoint in this axial clearance. The blood pump 500 has an axial back clearance between the left impeller 534 and the left pump housing 540 identified generally at "D1." As shown in FIG. 12, D1 is the clearance between the vanes 612 of the left impeller 534 and a back surface 578 of the left pump chamber 544, which may be defined at least partially by the stator assembly 520, the left pump housing 540, or both the stator assembly and the left pump housing. During operation of the pump 500, when the rotor assembly 530 moves axially relative to the stator assembly 520, the left impeller 534 moves axially within the left pump chamber 544.

The blood pump 500 has an axial front clearance between the right impeller 536 and the right pump housing 550, identified generally at "D2." The front clearance D2 is defined between the back plate 620 of the right impeller 536 and an annular ridge 630 on the right pump housing 550 where the volute surface 604 intersects the surface defining the chamber 608. The clearance D2 is indicative of the degree to which the vanes 622 of the second impeller 536 extend into the chamber 608 and out of the volute chamber 606. The clearance D2 is also indicative of the size of an annular opening or aperture 632 defined between the back plate 620 and the ridge 630. The aperture 632 defines the area through which the second impeller 536 pumps fluid through the volute chamber 606. As D2 decreases, the area of the aperture 632 decreases as the vanes 622 of the second impeller 536 move or extend further out of the volute chamber 606 into the chamber 608. Conversely, as D2 increases, the area of the aperture 632 increases as the vanes 622 of the second impeller 536 move or extend further out of the chamber 608 into the volute chamber 606.

In the configuration shown in FIG. 12, left pump 542 performance improves as D1 decreases and right pump 552 performance improves as D2 increases. During operation of the blood pump 500, the rotor assembly 530 can move or shuttle axially relative to the stator assembly 520 due to hydrodynamic pumping forces created by the left and right pumps 542 and 552. The rotor assembly 530 can move axially between a left position, in which D1 and D2 are maximum, and a right position, in which D1 and D2 are minimum.

When the rotor assembly 530 moves axially between the left and right positions, the configurations or geometries of the left and right pumps 542 and 552 are altered. As the axial position of the left impeller 534 changes, the clearance D1 between the left impeller and back surface 578 of the left pump housing 540 changes, which alters the configuration and geometry of the left pump 542 and left pump chamber 544. As the axial position of the right impeller 536 changes, the clearance D2 between the right impeller and the right pump housing 550, which alters the size of the aperture 632, the configuration and geometry of the right pump chamber 554, and the configuration or geometry of the right pump 552.

As the D1 clearance increases and the D2 clearance decreases, the first and second pumps 542 and 552 decrease hydraulic output. Thus, for a given pump speed, as the impellers 534 and 536 move toward the stator assembly 522 (i.e., reducing D1 and increasing D2), the pumps 542 and 552 increase hydraulic output and pressure and flow increase accordingly. Conversely, as the impellers 534 and 536 move away from the stator assembly 522 (i.e., increasing D1 and decreasing D2), the pumps 542 and 552 decrease hydraulic output and pressure and flow decrease accordingly.

It will thus be appreciated that, for the single motor, two-stage configuration of the blood pump 500 of the present invention, axial movement of the rotor assembly 530 that produces increased pressure and flow at the left pump stage 542 will also produce a decrease in pressure and flow at the right pump stage 552. Similarly, axial movement of the rotor assembly 530 that produces increased pressure and flow at the right pump stage 552 will also produce a decrease in pressure and flow at the left pump stage 542. From this, it follows that, for any given speed of the blood pump 500, the pressures and flows of the left and right pump stages 542 and 552 can be balanced if the axial position of the rotor assembly 530 relative to the stator assembly 520 is adjusted to the proper position.

Based on this principle, using the blood pump 500, systemic and pulmonary pressure and flow characteristics can be controlled through adjusting the axial position of the rotor assembly 530. In the embodiment of FIGS. 9-12, the axial position of the of the rotor assembly 530 and, thus, the geometry or configuration of the left and right pumps 542 and 552 can is controlled passively.

In the passive control configuration of the blood pump 500, the axial position of the rotor assembly 530 is controlled passively or inherently through hydraulic forces created by the left and right pumps 542 and 552 during operation.

Figure 13:
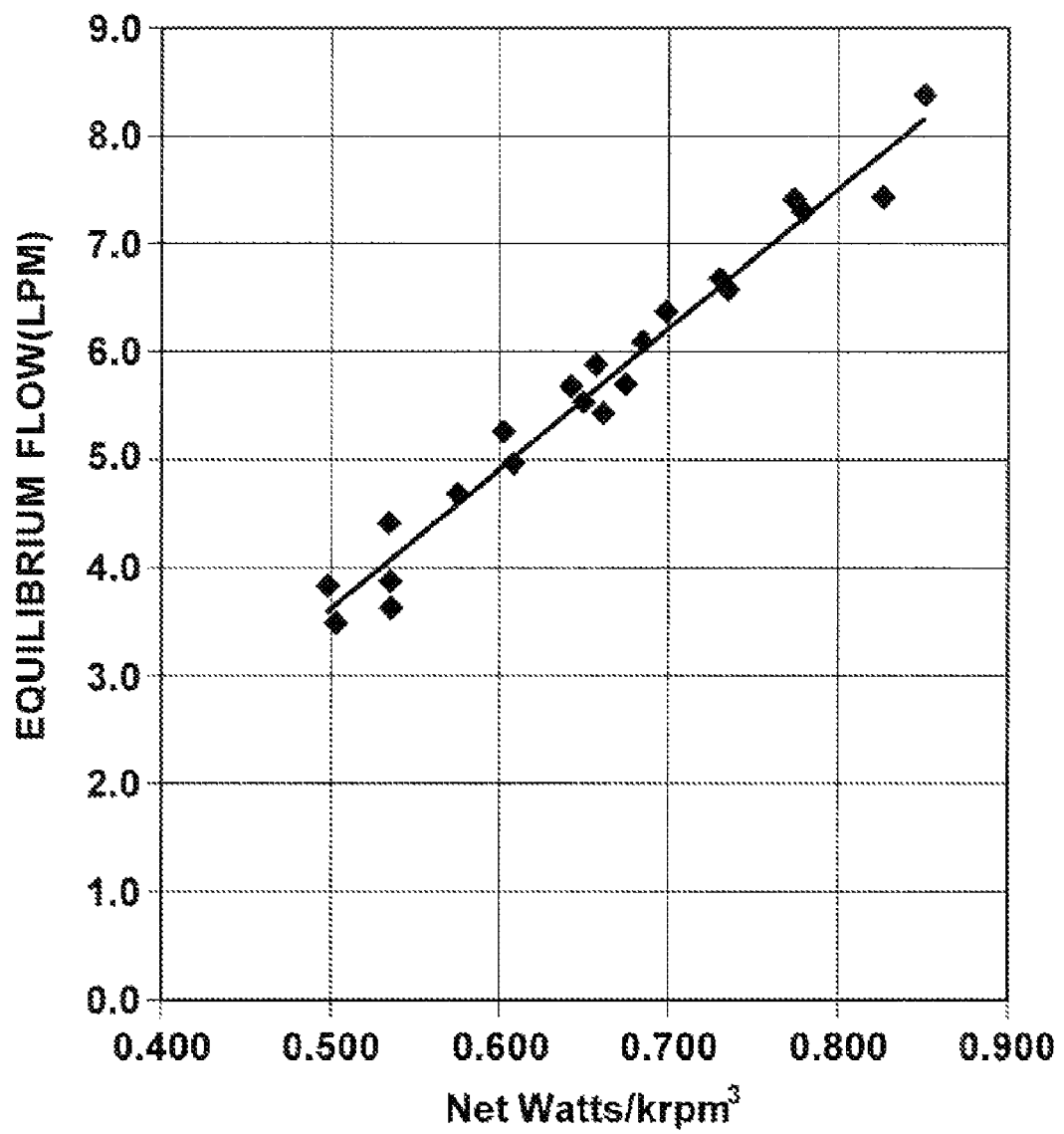
FIG. 13 is a graph illustrating characteristics of the blood pump of FIG. 9.

In operation, the control algorithm executed by the controller adjusts pump speed to provide a nominal systemic flow. Balanced systemic and pulmonary flows are achieved by adjusting of the axial position of the rotor assembly 530. The axial adjustments of the rotor assembly 530 occur inherently or automatically as a result of the configurations of the left and right impellers 534 and 536 and due to hydraulic pressures. Referring to FIG. 13, the control of speed of the pump 500 is based upon the characteristic mathematical relationship between speed, electric power consumption, and equilibrium output flow. In FIG. 13, net watts are equal to the electric power supplied to the motor minus the bearing drag power/motor efficiency and is calculated as the console power minus the power required to run the motor without impellers, where Systemic Vascular Resistance (SVR)=500-2000 dyne-sec/$cm^5$ and Pulmonary Vascular Resistance (PVR)=100-500 dyne-sec/$cm^5$. Also, in FIG. 13, KRPM is motor rpm/1000. The current response to speed pulses will also allow estimation of systemic vascular resistance, which can be correlated to the change in power consumption with speed.

Because the axial hydrodynamic forces acting on the back plate portions 610 and 620 of the impellers 534 and 536 are primarily those created by pump inlet pressures, the axial position of the rotor assembly 530 adjusts in response to pressure differentials between the left and right inlet portions 592 and 602. As the axial position of the rotor assembly 530 adjusts, the geometry and hydraulic performance of the left and right pumps 542 and 552 changes, as described above. This produces a corresponding change or adjustment in the outlet flows and pressures of the left and right pumps 542 and 552, trading pressure and flow performance between the two pumps. The blood pump 500 is thus configured with a self-adjusting rotor assembly 530 that helps balance pulmonary and systemic flows, as well as atrial pressures, through incremental changes the hydraulic performance of the left and right pumps 542 and 552.

When operating in high clearance, minimum pump performance occurs when the pumping vanes are centered in the axial clearance (front and back clearances equal). Therefore, performance can be modulated by moving the impellers 534 and 536 in either axial direction. Maximum performance for the left pump 542 occurs when back clearance D1 is minimum, while maximum performance for the right pump 552 occurs when front clearance D2 is maximum. The passive control implemented in the embodiment of FIGS. 9-12 modulates performance by adjusting the clearances D1 and D2. The advantage of using the back (inside) edges to modulate performance is that hydraulic forces operating on the rotating assembly can enforce the correct direction of axial movement for passive control, thereby eliminating the need for an active axial control system.

In the embodiment of FIGS. 9-12, the left pump 542 is configured to have a steep pressure rise vs. flow characteristic and also to regulate performance via the impeller vane clearance D1 such that the left pump output increases as the rotating assembly moves to the right as viewed in FIG. 12. The right pump 552 is configured to regulate performance by creating an aperture 632 that controls impeller vane discharge, decreasing output as the rotating assembly moves to the right (in FIG. 12), and increasing output as the rotating assembly moves to the left.

Advantageously, the configuration is self-regulating. In response to a changing vascular resistance, the rotating rotor assembly 530 moves in the direction of lowest inlet pressure to automatically correct imbalances between the inlet pressures at the left and right inlets 546 and 556. Thus, for example, in the case of inlet obstruction due to left atrial suction, the left inlet pressure drops and the rotating assembly moves to the left, i.e., in the direction of low pressure. This results in decreased left pump performance simultaneous with increased right pump performance, which automatically corrects the suction condition. The pump 500 would operate similarly and correspondingly to self regulate in the event of right atrial suction.

Figure 14:
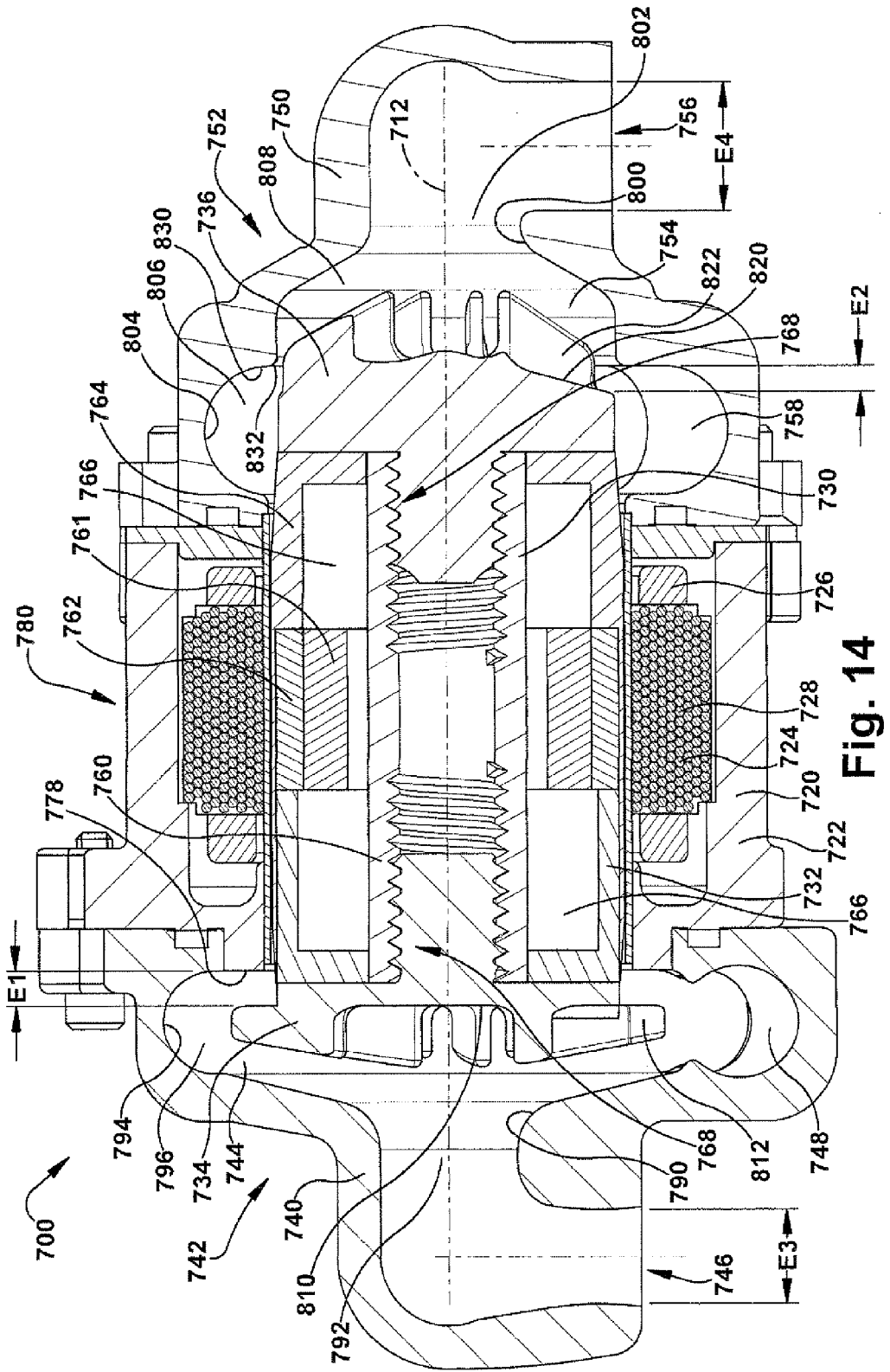
FIGS. 14-16 are sectional views illustrating a blood pump according to a fifth embodiment of the present invention.
Figure 15:
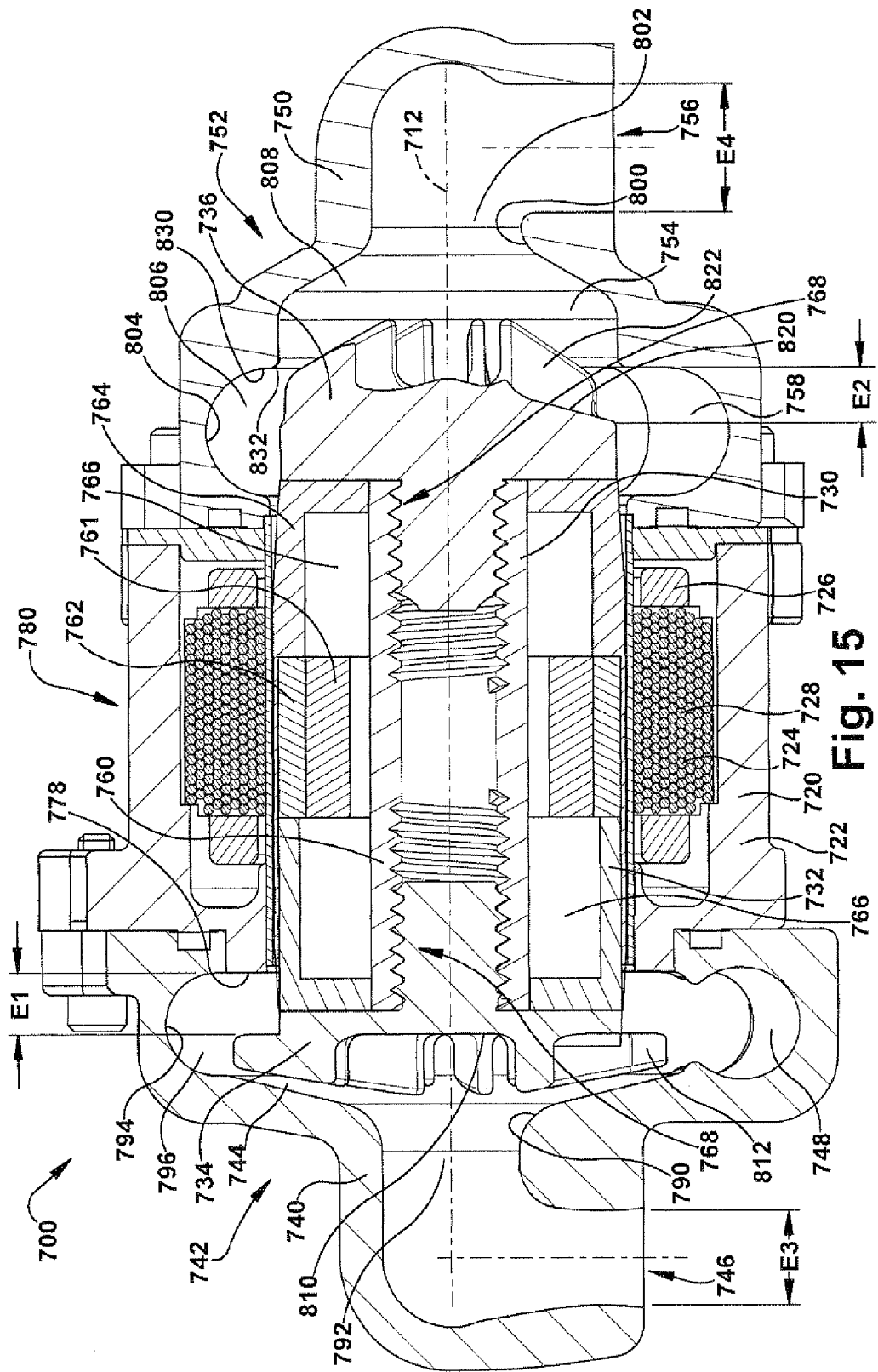
Figure 16:
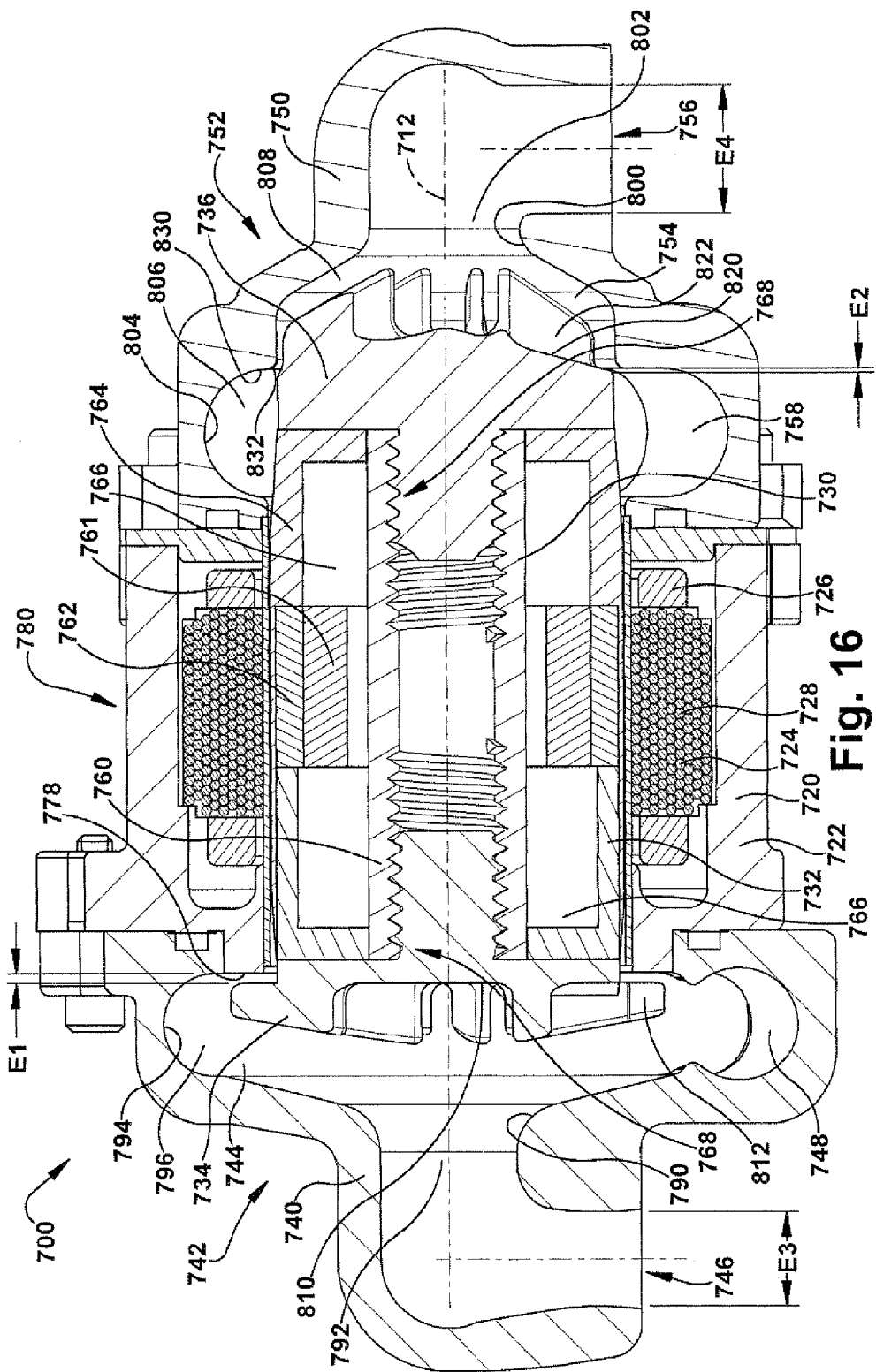

A blood pump 700 according to a fifth embodiment of the present invention is illustrated in FIGS. 14-16. The blood pump 700 of FIGS. 14-16 has a configuration that is similar to the embodiments of FIGS. 9-12 and has a two-stage or dual centrifugal pump configuration. The blood pump 700 may thus be configured for use as a total artificial heart (TAH) device. The blood pump 700 could, however, be suitable for non-TAH implementations, such as biventricular support or any implementation in which a dual or two stage fluid handling pump with pressure balancing features is desired.

FIGS. 14-16 illustrate the blood pump 700 in different positions that are described in detail below. Referring to FIG. 14, the blood pump 700 includes a stator assembly 720, a rotor assembly 730, a left pump housing 740, and a right pump housing 750. In an assembled condition of the blood pump 700, the rotor assembly 730 is supported by the stator assembly 720 for rotation about an axis 712. The pump housings 740 and 750 are fixed to the stator assembly 720 to enclose the rotor assembly 730. The rotor assembly 730 includes a motor rotor 732, a first or left impeller 734, and a second or right impeller 736.

The motor rotor 732 includes a core 760 surrounded or otherwise encased in a shell or casing 764 upon which a ring-shaped permanent magnet 762 is mounted. The core 760 may be constructed of a low density magnetically permeable material and may include hollow cavities 766 that help make the rotor assembly 730 a neutral buoyancy rotating assembly that is insensitive to the attitude of the pump 700. The core 760 supports a magnet core 761 constructed, for example, of steel, that in turn supports the magnet 762 for rotation with the motor rotor 732. The left and right impellers 734 and 736 may be secured to the core 760 by known means, such as adhesives, mechanical fasteners, or, could be formed as a single piece of material with the shell 764 via molding. In the embodiment illustrated in FIGS. 14-16, the impellers 734 and 736 are secured to the core 760 via threaded connections 768.

The stator assembly 720 includes a stator housing 722 that supports a motor stator 724. The motor stator 724 includes a stator core and motor windings, illustrated schematically at 726 and 728, respectively in FIG. 14. The motor windings 728 are electrically connected to a control cable (not shown). The rotor magnet 762 is shorter than the motor windings 728 to allow a controlled amount of free axial movement of the rotor assembly 730.

The blood pump 700, when assembled, includes a centrifugal first or left pumping stage or pump 742. The left pump 742 includes the left impeller 734 and a left pump chamber 744 in which the left impeller is disposed. The left pump chamber 744 is defined, at least partially, by the left pump housing 740 and the stator assembly 720. The left pump 742 also includes a left pump inlet 746 and a left pump outlet 748 that, in the illustrated embodiment, are formed as integral portions of the left pump housing 740. The left pump housing 740 includes an inlet surface 790 that helps define an inlet portion 792 of the left pump chamber 744 in fluid communication with the inlet 746. The left pump housing 740 also includes a volute surface 794 that helps define a volute portion 796 of the left pump chamber 744 in fluid communication with the outlet 748.

The blood pump 700, when assembled, also includes a centrifugal second or right pumping stage or pump 752. The right pump 752 includes the right impeller 736 and a right pump chamber 754 in which the right impeller is disposed. The right pump chamber 754 is defined, at least partially, by the right pump housing 750 and the stator assembly 720. The right pump 752 also includes a right pump inlet 756 and a right pump outlet 758 that, in the illustrated embodiment, are formed as integral portions of the right pump housing 750. The right pump housing 750 includes an inlet surface 800 that helps define an inlet portion 802 of the right pump chamber 754 in fluid communication with the inlet 756. The right pump housing 750 also includes a volute surface 804 that helps define a volute portion 806 of the right pump chamber 754 in fluid communication with the outlet 758. The right pump housing 750 further includes a chamber 808 adjacent the volute portion 806.

The motor rotor 732 and motor stator 724 help define a motor 780 of the blood pump 700 that drives the left and right pumps 742 and 752. The motor 780 may be any type of electric motor suited to drive the pumps 742 and 752 and deliver the desired performance characteristics. For example, in the illustrated embodiment, the motor 780 may have a single phase or multi-phase brushless, sensorless DC motor configuration. A motor controller (not shown) is operative to excite the phase windings 728 of the motor 780 to achieve desired performance of the motor portion, such as motor speed or current. For example, the motor controller may apply pulse width modulated voltage to the motor phases in order to achieve the desired motor/pump performance.

The first impeller 734 includes a back plate 810 and a plurality of vanes 812 that extend radially from the rotor 730. The vanes 812 may include first or primary vanes and second or splitter vanes. The vanes 812 may be configured with a low incidence inlet and a radial discharge. The second impeller 736 includes a back plate 820 and a plurality of vanes 822 that extend radially along the end face of the rotor 730. The vanes 822 may, for example, include first or primary vanes and second or splitter vanes that may be configured with a low incidence inlet and a radial discharge. Those skilled in the art will appreciate that the impellers 734 and 736 could have alternative configurations.

The back plates 810 and 820 are aligned axially with the inlet portions 792 and 802 of the left and right pump chambers 744 and 754, respectively. Therefore, fluid pressures acting on the back plates 810 and 820 are primarily inlet pressures and thus exert forces on the rotor assembly 730 that are primarily axial, i.e., parallel to the axis 712. Outlet pressures produced by the blood pump 700 are generated primarily at the end portions of the vanes 812 and 822.

During operation of the blood pump 700, the rotor assembly 730 rotates about the axis 712 relative to the stator assembly 720. The rotor assembly 730 is supported or rides on a hydrodynamic or fluid film bearing formed by the pumped fluid, i.e., blood. Alternatively, the blood pump 700 could include other types of bearing features, such as mechanical bearings or bearing surfaces formed from or coated with low friction materials, for facilitating rotation of the rotor assembly 730. As a further alternative, the rotor assembly 730 could be magnetically suspended.

The materials used to construct the blood pump 700 may be formed from materials conducive to blood pumping implementations. For example, portions of the blood pump 700 that are exposed to blood flow during use, such as the impellers 734 and 736 and pump housings 740 and 750, may be formed from, coated, or encased in a biocompatible material, such as stainless steel, titanium, ceramics, polymeric materials, composite materials, or a combination of these materials. Surfaces or portions of the blood pump 700 that may contact each other during use, such as the left impeller 734 and pump housing 740, the right impeller 736 and pump housing 750, or the rotor casing 764, may also be formed or coated with low friction materials, such as a fluorocarbon polymer coatings, diamond-like carbon coatings, ceramics, titanium, and diamond coated titanium.

According to the present invention, the blood pump 700 is configured with a clearance that permits axial movement (left/right movement as shown in FIGS. 14-16) of the rotor assembly 730 relative to the stator assembly 720 during operation of the pump. In FIG. 14, the rotor assembly 730 is in a center position about midpoint in this axial clearance. FIG. 15 illustrates the rotor assembly 730 in a full-left position of this axial clearance. FIG. 16 illustrates the rotor assembly 730 in a full-right position of this axial clearance.

The axial clearance of the blood pump 700 creates an axial back clearance between the left impeller 734 and the left pump housing 740 identified generally at "E1." As shown in FIG. 14, E1 is the clearance between the vanes 812 of the left impeller 734 and a back surface 778 of the left pump chamber 744, which may be defined at least partially by the stator assembly 720, the left pump housing 740, or both the stator assembly and the left pump housing. During operation of the pump 700, when the rotor assembly 730 moves axially relative to the stator assembly 720, the left impeller 734 moves axially within the left pump chamber 744. In the embodiment illustrated in FIGS. 14-16, the left impeller 734 is positioned within the volute portion 796 of the left pump chamber 744 throughout the range of axial movement of the rotor assembly 730.

The axial clearance of the blood pump 700 creates an axial front clearance between the right impeller 736 and the right pump housing 750, identified generally at "E2." The front clearance E2 is defined between the back plate 820 of the right impeller 736 and an annular ridge 830 on the right pump housing 750 where the volute surface 804 intersects the surface defining the chamber 808. The clearance E2 is indicative of the degree to which the vanes 822 of the second impeller 736 extend into the chamber 808 and out of the volute chamber 806. The clearance E2 is also indicative of the size of an annular opening or aperture 832 defined between the back plate 820 and the ridge 830. The aperture 832 defines the area through which the second impeller 736 pumps fluid through the volute chamber 806. As E2 decreases, the area of the aperture 832 decreases as the vanes 822 of the second impeller 736 move or extend further out of the volute chamber 806 into the chamber 808. Conversely, as E2 increases, the area of the aperture 832 increases as the vanes 822 of the second impeller 736 move or extend further out of the chamber 808 into the volute chamber 806.

During operation of the pump 700, the rotor assembly 730 can move or shuttle freely in axial directions relative to the stator assembly 720 due to hydrodynamic pumping forces created by the left and right pumps. The motor windings 728, being longer than the rotor magnet 762, do not exert an axial pull on the rotor 732, and therefore do not resist axially shuttling of the rotor, as long as the rotor magnet is positioned within the length of the windings. If the rotor 732 attempts to travel axially beyond the length of the windings 728, it is magnetically constrained in order to prevent contact between the rotor and the pump housings 740 and 750. Additionally, the rotor assembly 730, being neutrally buoyant in blood, helps make the pump 700 insensitive to positional or attitudinal changes during use.

When shuttling due to hydrodynamic pumping forces, the rotor assembly 730 can move axially between the full-left position (FIG. 15), in which E1 and E2 are maximum, and the full-right position (FIG. 16), in which E1 and E2 are minimum. When the rotor assembly 730 moves axially between the left and right positions, the configurations or geometries of the left and right pumps 742 and 752 can change. The degree to which the configurations or geometries of the left and right pumps 742 and 752 change in response to this axial shuttling depends on the configuration of the pumping chambers 744 and 754, the configuration of the impellers 734 and 736, and the relative spatial relationships of these parts when the rotor assembly 730 moves axially.

Adjusting the geometries or configurations of the left and right pumps 742 and 752 results in a corresponding adjustment of the hydraulic performance characteristics of the pumps. By "hydraulic performance" it is meant to refer to a term of art that is well-known to those having skill in the art of fluid dynamics and pump design. The hydraulic performance of a centrifugal pump is defined by the relationship, for that particular pump, between volumetric flow, differential pressure (inlet-outlet pressure rise), and pump speed. That is, measuring pump hydraulic performance is based on the principle that for any given pump architecture, at a given pump speed and system pressure, the pump will produce a specific volumetric flow rate. This allows hydraulic performance to be a standard, fundamental benchmark used to quantify and compare centrifugal pumps.

Those skilled in the art will appreciate that, in a TAH scenario, it is critical to balance pulmonary and systemic arterial blood flows and atrial pressures. For example, if the right pump 752 delivers blood at a higher flow rate than the left pump 742, blood may accumulate in the lungs. As another example, if the left pump 742 delivers blood at a higher flow rate than the right pump 752, blood may accumulate in the liver and other internal organs, leading to organ failure. The goal for the blood pump 700 is thus to balance pulmonary and systemic arterial blood flows and atrial pressures. According to the present invention, the blood pump 700 balances systemic and pulmonary atrial pressures and arterial flow rates by adjusting the geometry or configuration of the left (systemic) pump 742 and right (pulmonary) pump 752.

Based on the above, the blood pump 700 is configured to control systemic and pulmonary pressure and flow characteristics through adjusting the axial position of the rotor assembly 730 in order to adjust the hydraulic performance characteristics of the left and right pumps 742 and 752. In the embodiment of FIGS. 14-16, the axial position of the of the rotor assembly 730 and, thus, the geometry or configuration of the left and right pumps 742 and 752 is controlled passively. In this passive control configuration of the blood pump 700, the axial position of the rotor assembly 730 is controlled inherently or automatically by the hydraulic forces created by the left and right pumps 742 and 752 during operation.

Those skilled in the art will appreciate the fact that, in the human body, normal systemic blood pressure is more than three times normal pulmonary blood pressure. Thus, in a total artificial heart (TAH) environment, the left (systemic) pump 742 performs more than three times the amount of work than that performed by the right (pulmonary) pump 752. Therefore, one skilled in the art will appreciate that it may be desirable, for the sake of conserving power and efficiency, to adjust the hydraulic performance of the right pump 752 while maintaining relatively consistent left pump 742 performance since the right pump 752 performs substantially less work than the left pump 742. According to the present invention, the pump 700 of FIGS. 14-16 achieves, at least substantially, this purpose.

In operation, the control algorithm executed by the controller adjusts pump speed to provide a nominal systemic flow. Balanced systemic and pulmonary flows are achieved by adjusting the axial position of the rotor assembly 730. Axial movement of the rotor assembly 730 to the right as viewed in FIGS. 14-16 decreases pressure and flow at the right pump 752. Axial movement of the rotor assembly 730 to the left as viewed in FIGS. 14-16 produces increased pressure and flow at the right pump 752. From this, it follows that, for any given speed of the pump 700, the pressures and flows of the left and right pumps 742 and 752 can be balanced if the axial position of the rotor assembly 730 relative to the stator assembly 720 is adjusted to the proper position. Based on this principle, the pump 700 can control relative systemic and pulmonary pressure and flow characteristics through adjusting the axial position of the rotor assembly 730.

Because the axial hydrodynamic forces acting on the back plate portions 810 and 820 of the impellers 734 and 736 are primarily those created by pump inlet pressures, the axial position of the rotor assembly 730 adjusts in response to pressure differentials between the left and right inlet portions 792 and 802. As the axial position of the rotor assembly 730 adjusts, the geometry and hydraulic performance of the right pump 752 changes, as described above. This produces a corresponding change or adjustment in the outlet flows and pressures of the right pump 752 until the pressures at the inlets 792 and 802 are balanced. The blood pump 700 is thus configured with a self-adjusting rotor assembly 730 that helps balance pulmonary and systemic flows, as well as atrial pressures, through incremental changes in the hydraulic performance of the right pump 752.

Advantageously, the configuration is self-regulating. In response to a changing vascular resistance, the rotating rotor assembly 730 moves in the direction of lowest inlet pressure to automatically adjust the geometries of the left and right pumps 742 and 752, which adjusts the relative hydraulic performance characteristics of the pumps and thereby corrects imbalances between the inlet pressures at the left and right inlets 746 and 756. Because unbalanced atrial pressures are the result of imbalanced flows, drawing the pressures to balance also results in balanced flows. Thus, for example, in the case of inlet obstruction due to left atrial suction, the left inlet pressure drops and the rotating assembly moves to the left, i.e., in the direction of low pressure. This results in increased right pump performance, which fills the left atrium and thereby automatically corrects the suction condition. In the case of right suction, the rotating assembly would move to the right, closing the aperture 832, thereby reducing the right pump 752 performance and automatically correcting the right suction condition.

Those skilled in the art will appreciate that the degree or manner in which the configurations or geometries of the left and right pumps 742 and 752 change in response to axial shuttling of the rotor assembly 730 depends on the individual configurations of the respective pumping housings 740 and 750 and impellers 734 and 736 and on the spatial relationships of these structures. Therefore, the degree or manner in which the hydraulic performance characteristics of the left and right pumps 742 and 752 change in response to axial shuttling of the rotor assembly 730 also depend on these characteristics. Further, the degree to which the configuration, geometry, and hydraulic performance of the left and right pumps 742 and 752 are adjusted can be tailored individually to the pumps. For example, in the embodiment of the present invention illustrated in FIGS. 14-16, the housing 740 and impeller 734 of the left pump 742 are configured to minimally adjust the hydraulic performance characteristics of the left pump in response to axial shuttling of the rotor assembly 730. Conversely, the housing 750 and impeller 736 of the right pump 752 are configured to substantially adjust the hydraulic performance characteristics of the right pump in response to axial shuttling of the rotor assembly 730.

Regarding the left pump 742, according to the present invention, the left impeller 734 is positioned within the volute portion 796 throughout the entire range of motion. As the rotor assembly 730 shuttles axially from the full-left position of FIG. 15 to the full-right position of FIG. 16, a clearance is maintained between the left impeller 734 and the left housing. As a result, the geometry and the hydraulic performance of the left pump 742 remains relatively constant as the rotor assembly 730 shuttles between these two extremes.

Regarding the right pump 752, as the rotor assembly 730 shuttles axially, the right impeller 736 moves between the volute portion chamber 806 and chamber 808. Blood entering the right pump 752 must pass through chamber 808 into the volute portion 806 via the aperture 832. The size of the aperture 832, defined by the clearance E2, adjusts depending on the axial position of the impeller. As this clearance E2 increases, the portion of the right impeller 736 positioned in the volute portion 806 versus the portion positioned in the chamber 808 increases and the hydraulic output of the right pump 752 increases. As this clearance E2 decreases, the portion of the right impeller 736 positioned in the volute portion 806 versus the portion positioned in the chamber 808 decreases and the hydraulic output of the right pump 752 decreases. Thus, as the rotor assembly 730 shuttles between the full-left position of FIG. 15 to the full-right position of FIG. 16, the right impeller 736 goes from being positioned fully within the volute portion 806 to fully within the chamber 808. Since the portion of the right impeller 736 positioned in the chamber 808 is substantially inhibited from contributing to the pumping action of the right pump 752, the change in the configuration or geometry of the right pump varies substantially as the rotor assembly 730 shuttles axially. It is due to this that the hydraulic performance of the right pump 752 varies substantially as the rotor assembly 730 shuttles between these two extremes.

When the inlet (atrial) pressure at the left pump 742 is higher than the inlet (atrial) pressure at the right pump 752 (for example, due to right over pumping or left under pumping), the rotor assembly 730 is shifted by hydraulic forces to the right, thereby closing the right pump aperture 832 and decreasing the right pump hydraulic performance. Conversely, when the inlet (atrial) pressure at the left pump 742 is lower than the inlet (atrial) pressure at the right pump 752 (for example, due to right under pumping or left over pumping), the rotor assembly 730 is shifted by hydraulic forces to the left, thereby opening the right pump aperture 832 and increasing the right pump hydraulic performance. From this, it follows that, for any given speed of the blood pump 700, the pressures and flows of the left and right pump stages 742 and 752 can be balanced if the axial position of the rotor assembly 730 relative to the stator assembly 720 adjusts to the proper position.

Figure 17:
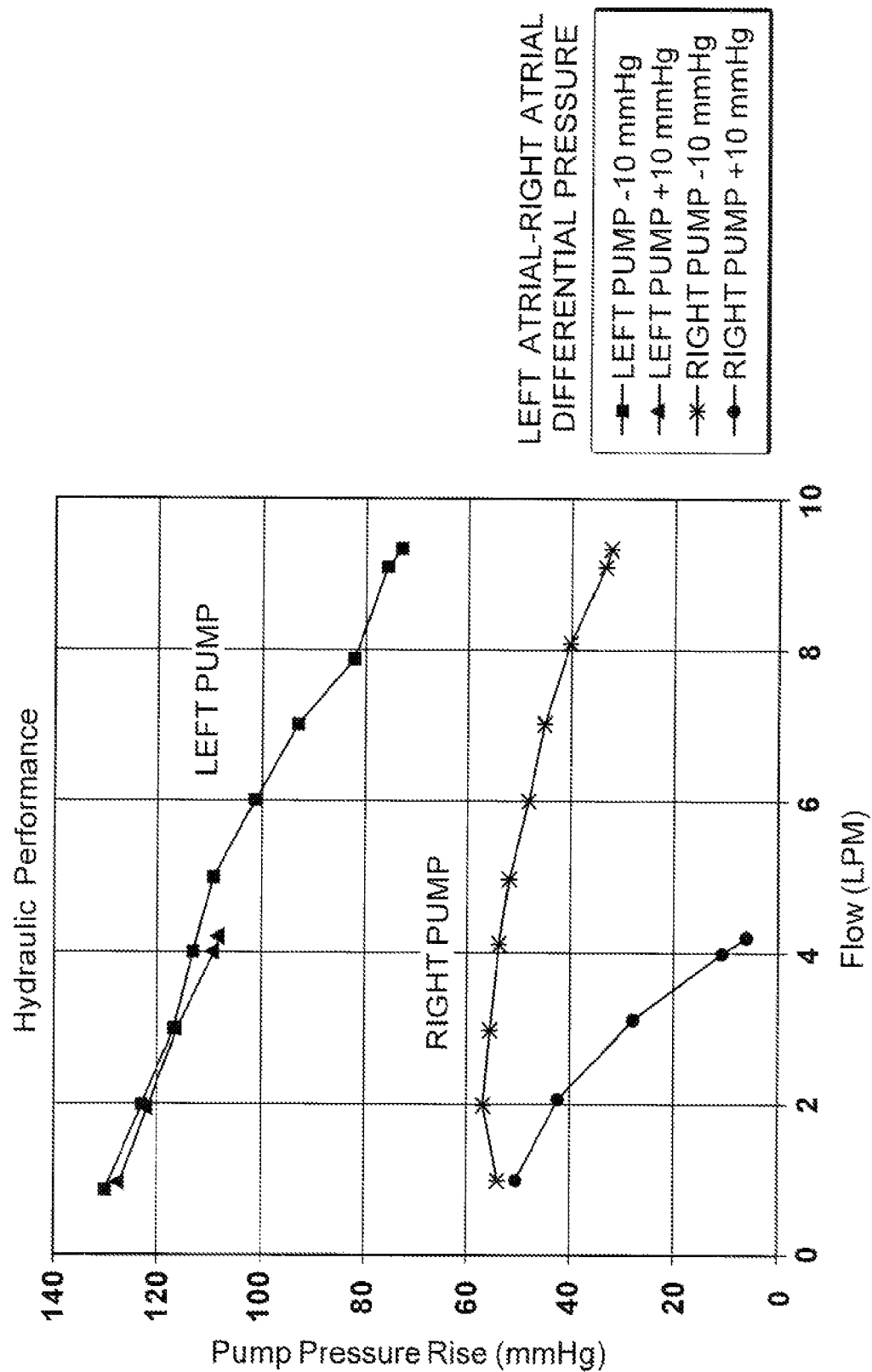
FIG. 17 is a graph illustrating hydraulic performance characteristics of the blood pump of FIGS. 14-16.

To illustrate how the left and right pumps 742 and 752 respond to varying inlet (atrial) pressure differentials, the hydraulic performance of the left and right pumps 742 and 752 is illustrated in FIG. 17. FIG. 17 illustrates a chart or diagram that plots pressure vs. flow curves for the left and right pumps 742 and 752 for a given pump speed of 2700 rpm pumping a solution of Water and Glycerin at a specific gravity of about 1.06 to mimic pumping blood. FIG. 17 illustrates the hydraulic performance of the left and right pumps 742 and 752 equal flow of the pumps with inlet (atrial) pressure differentials that range from −10 to +10 mmHg. As shown in FIG. 17, the hydraulic performance of the left pump 742 varies very little between these extremes. The hydraulic performance of the right pump, however, varies greatly and therefore accounts for a majority of the hydraulic performance regulation of the pump 700.

Referring to FIG. 17, by way of example illustration, consider a scenario in which the inlet pressure at the left pump 742 is 6 mmHg higher than the inlet pressure at the right pump 752. This could be the result, for example, of a physiological change that creates a variation in fluid flow resistance in one or both of the systemic and pulmonary systems. In this situation, the left and right pumps 742 and 752 are operating on hydraulic performance curves that lie between the respective extremes in FIG. 17. Since axial shifting produces relatively little change in the hydraulic performance of the left pump 742, the majority of the pressure compensation is seen at the right pump 752. Since the right pump 752 in this scenario begins with an inlet pressure deficiency (−6 mmHg), the curve (not shown) upon which the right pump is operating would shift downward as viewed in FIG. 17. As a result, the hydraulic performance of the right pump would decrease, causing a resultant increase in inlet pressure at the right pump, moving the inlet pressure differential toward zero, thereby correcting the atrial pressure imbalance.

Figure 18:
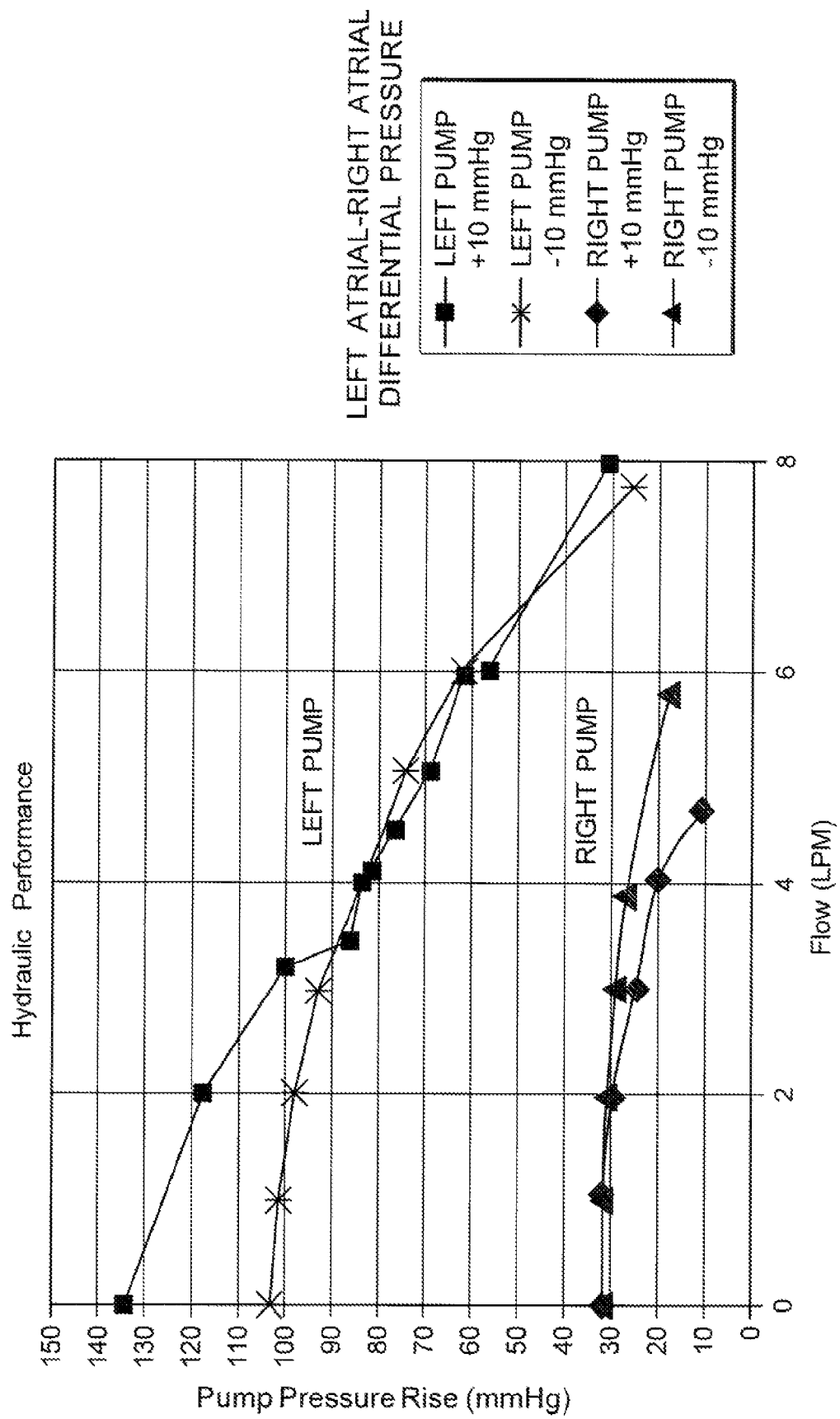
FIG. 18 is a graph illustrating hydraulic performance characteristics of the blood pump of FIG. 12.

Comparing the chart of FIG. 17 to the charts of FIGS. 18 and 19 illustrates how the different pump geometries result in different hydraulic performance characteristics of the pumps. FIG. 18 illustrates the hydraulic performance characteristics of the pump 500 of FIG. 12. In FIG. 18, a chart or diagram plots pressure vs. flow curves for the left and right pumps 542 and 552 for a given pump speed of 2100 rpm pumping a solution of Water and Glycerin at a specific gravity of about 1.06 to mimic pumping blood. FIG. 18 illustrates the hydraulic performance of the left and right pumps 542 and 552 equal flow of the pumps with inlet (atrial) pressure differentials that range from −10 to +10 mmHg.

FIG. 18 illustrates that the hydraulic performance of the left pump 542 and right pump 552 both vary between these extremes and thus both contribute to the hydraulic performance regulation of the pump 500. As illustrated in FIG. 18, there is a threshold effect for the left pump 542 (at 3.5 LPM, 2100 rpm), but it is only at low flows. So, in the case of extreme operating conditions, the left pump performance will increase as needed to keep a minimum flow for a given speed.

FIG. 19 illustrates the hydraulic performance characteristics of the pump 10 of FIG. 2. In FIG. 19, a chart or diagram plots pressure vs. flow curves for the left and right pumps 42 and 52 for a given pump speed of 1500 rpm pumping a solution of Water and Glycerin at a specific gravity of about 1.06 to mimic pumping blood. FIG. 19 illustrates the hydraulic performance of the left and right pumps 42 and 52 for extreme left and right axial positions of the rotating assembly.

FIG. 19 illustrates that the hydraulic performance of both the left pump 42 provides essentially all of the performance variation and regulation of the pump 10. As A1 becomes small, the performance transforms at a certain flow rate, proportional to speed. FIG. 19 illustrates that, for the configuration of the pump 10 of FIG. 2, the left pump 42 transitions from exhibiting centrifugal pump characteristics to regenerative pump characteristics at a certain value of flow coefficient [flow/speed]. If the left atrial pressure is high due to low relative left performance, the rotating assembly moves to the right, A1 becomes smaller, and the performance of the left pump increases. Because of the threshold effect shown in FIG. 19, it will automatically tend to hold the threshold flow (6 LPM at 1500 rpm). Therefore, flow tends to be both balanced and proportional to speed.

Those skilled in the art will appreciate that it may be desirable for nominal operation of the pump 700 to be biased to run with the left atrial pressure slightly higher, e.g., 3 mmHg higher, than right inlet pressure so as to be consistent with normal hemodynamic values of the human body. According to the present invention, this is achieved by adjusting the cross-sectional area of the left pump inlet 746 to be smaller than the cross-sectional area of the right pump inlet 756 in order to create a pressure drop at the left pump 742. As shown in FIGS. 14-16, the left pump inlet 746 has a diameter E3 that is smaller than the diameter E4 of the right pump inlet 756. As a result of the pressure drop created by the reduced inlet diameter at the left pump 742, atrial pressures exerted on or "seen" at the left impeller 734 pump are lower (e.g., 3 mmHg lower) than actual at nominal target flow rates (5-6 lpm). This causes the rotor assembly 730 to overcompensate by over-shifting to the left and under-shifting to the right, as viewed in FIGS. 14-16. Thus, when the pump reaches equilibrium where the pump inlet differential pressure is 0 mmHg, the atrial pressure differential will actually be approximately +3 mmHg in favor of the left. The added pressure drop at the left inlet also aids with opening the right pump aperture 832 more fully at high flows.

From the above description of the invention, those skilled in the art will perceive improvements, changes and modifications. Such improvements, changes and modifications within the skill of the art are intended to be covered by the appended claims.

Having described the invention, the following is claimed:
1. A pump comprising:
   a housing;
   a stator supported in the housing, the stator comprising a stator core and motor windings wrapped around the stator core, the core and windings having a cylindrical configuration defining a cylindrical space having a central axis, the stator core having an axial length measured along the axis; and
   a rotor assembly comprising:
   a cylindrical rotor supported in the cylindrical space housing for rotation relative to the stator about the axis;
   a first impeller operatively coupled to a first axial end of the rotor for rotation with the rotor about the axis; and
   a second impeller operatively coupled to a second axial end of the rotor, opposite the first axial end, for rotation with the rotor about the axis;
   wherein the rotor comprises a motor magnet that has an axial length that is shorter than the axial length of the stator core, the rotor assembly being free to move along the axis relative to the housing within the axial length of the stator core to adjust hydraulic performance characteristics of the pump.

2. The pump recited in claim 1, wherein the rotor is of neutral buoyancy in blood.

3. The pump recited in claim 1, wherein the stator core comprises axial constraints that permit free axial movement of the motor magnet while positioned within the axial length of the stator core, the axial constraint preventing axial travel of the motor magnet beyond the axial length of the stator core.

4. The pump recited in claim 1, wherein the pump comprises:
   a first pumping stage comprising a first pump housing part that helps define a first pumping chamber in which the first impeller is supported for rotation about the axis, the first impeller being movable along the axis relative to the first pump housing part; and
   a second pumping stage comprising a second pump housing part that helps define a second pumping chamber in which the second impeller is supported for rotation about the axis, the second impeller being movable along the axis relative to the second pump housing part;
   the first and second impellers when moved along the axis with the rotor assembly moving axially relative to the first and second pump housing parts to adjust the hydraulic performance characteristics of the first and second pumping stages.

5. The pump recited in claim 4, wherein the first pump housing part and the first impeller are configured to respond to axial movement of the rotor assembly by adjusting the hydraulic performance characteristics of the first pumping stage; and
   the second pump housing part and the second impeller are configured to respond to axial movement of the rotor assembly by adjusting the hydraulic performance characteristics of the second pumping stage.

6. The pump recited in claim 4, wherein the configurations of the first and second pump housing parts and the first and second impellers are selected such that the hydraulic performance characteristics of the first pumping stage adjust in response to axial movement of the rotor assembly in a manner different than the manner in which the hydraulic performance characteristics of the second pumping stage adjust in response to the same axial movement of the rotor assembly.

7. The pump recited in claim 4, wherein at least one of the first and second pumping stages comprises a pumping chamber and an adjacent chamber in fluid communication with the pumping chamber, the impeller associated with the at least one pumping stage having at least a portion movable into and out of the adjacent chamber from the pumping chamber in response to axial movement of the rotor assembly.

8. The pump recited in claim 7, wherein the adjacent chamber is positioned between the pumping chamber and an inlet of the at least one pumping stage, the associated pumping stage comprising an aperture defined between the associated impeller and a portion of a sidewall of the associated pump housing part at or near the interface between the pumping chamber and the adjacent chamber, the aperture having a size that varies depending on the axial position of the associated impeller.

9. The pump recited in claim 7, wherein the portion of the associated impeller positioned in the adjacent chamber is at least substantially inhibited from pumping fluid through the associated pumping stage.

10. The pump recited in claim 1, wherein the first and second impellers each comprise a back plate and a plurality of vanes extending radially from the back plate, the vanes having end portions that extend radially beyond an outer periphery of the back plate.

11. The pump recited in claim 10, wherein:
the first back plate is aligned axially with and directly faces a first pump inlet of the first pump housing part such that fluid pressures acting on the first back plate are primarily inlet pressures that exert axial hydraulic forces on the rotor assembly in a first direction along the axis; and
the second back plate is aligned axially with and directly faces a second pump inlet of the second pump housing part such that fluid pressures acting on the second back plate are primarily inlet pressures that exert axial hydraulic forces on the rotor assembly in a second direction along the axis opposite the first direction.

12. The pump recited in claim 11, wherein the axial position of the rotor assembly in the housing varies in response to the axial hydraulic forces exerted on the rotor assembly.

13. The pump recited in claim 11, wherein the pump is configured such that for a given pump speed, there is an axial position of the rotor assembly at which the axial forces exerted on the first and second back plates are equal and opposite.

14. The pump recited in claim 10, wherein:
outlet pressures produced by the first impeller are generated primarily at the end portions of the vanes of the first impeller; and
outlet pressures produced by the second impeller are generated primarily at the end portions of the vanes of the second impeller.

15. The pump recited in claim 10, wherein the vanes of the first and second impellers comprise primary vanes and splitter vanes with low incidence inlets and radial discharges.

16. The pump recited in claim 1, further comprising an actuator actuatable to adjust the axial position of the rotor assembly to achieve desired hydraulic performance characteristics of the pump.

17. The pump recited in claim 16, wherein the actuator comprises an electric solenoid.

18. The pump recited in claim 1, wherein the pump is configured such that fluid inlet pressures acting on the first impeller exerts an axial force on the rotor assembly in a first direction along the axis and fluid inlet pressures acting on the second impeller exerts an axial force on the rotor assembly in a second direction along the axis, opposite the first direction.

19. The pump recited in claim 18, wherein the axial forces exerted on the rotor assembly by the fluid inlet pressures acting on the first and second impellers adjusts the axial position of the rotor assembly to help balance the fluid inlet pressures acting on the first and second impellers.

20. The pump recited in claim 1, further comprising a first inlet associated with the first impeller, and a second inlet associated with the second impeller, the first and second inlets having different internal diameters.

21. The pump recited in claim 20, wherein the internal diameters of the first and second inlets are selected to be of different sizes that create differential inlet pressure drops to bias the axial forces acting on the first and second impellers.

22. A total artificial heart pump comprising:
a left pump stage with an inlet for receiving left atrial blood flow and an outlet for discharging systemic blood flow via the aorta;
a right pump stage with an inlet for receiving right atrial blood flow and an outlet for discharging pulmonary blood flow via the pulmonary artery;
a motor comprising a stator and a rotor for rotating a left impeller of the left pump stage and a right impeller of the right pump stage, the motor being configured to permit the rotor to move axially relative to the stator during operation of the pump;
the pump being adapted such that differentials in left and right atrial pressures adjust the axial position of the rotor which adjusts the relative hydraulic performance characteristics of the left and right pump stages to balance the left and right atrial pressures and balance the systemic and pulmonary blood flows.

23. The total artificial heart pump recited in claim 22, wherein the left pump stage further comprises a left pump housing, the left pump housing and left impeller being configured to adjust the hydraulic performance characteristics of the left pump stage depending on the axial position of the left impeller in the left pump housing.

24. The total artificial heart pump recited in claim 22, wherein the right pump stage further comprises a right pump housing, the right pump housing and right impeller being configured to adjust the hydraulic performance characteristics of the right pump stage depending on the axial position of the right impeller in the right pump housing.

25. The total artificial heart pump recited in claim 22, wherein the left pump stage is configured to urge the rotor in a first axial direction relative to the stator in response to left atrial pressures acting on the left impeller, the right pump stage being configured to urge the rotor in a second axial direction relative to the stator opposite the first axial direction in response to right atrial pressures acting on the right impeller.

26. The pump recited in claim 22, wherein the internal diameters of the left pump stage inlet and the right pump stage inlet are selected to create differential inlet pressure drops to bias the axial forces acting on the left and right impellers.

* * * * *